US006783733B2

(12) United States Patent
Bogen et al.

(10) Patent No.: US 6,783,733 B2
(45) Date of Patent: Aug. 31, 2004

(54) RANDOM ACCESS SLIDE STAINER WITH INDEPENDENT SLIDE HEATING REGULATION

(75) Inventors: Steven A. Bogen, Sharon, MA (US); Herbert H. Loeffler, Arlington, MA (US); John A. Purbrick, Arlington, MA (US)

(73) Assignee: CytoLogix Corporation, Cambridge, MA (US)

( * ) Notice: Subject to any disclaimer, the term of this patent is extended or adjusted under 35 U.S.C. 154(b) by 274 days.

(21) Appl. No.: 10/027,746

(22) Filed: Dec. 20, 2001

(65) Prior Publication Data

US 2002/0054830 A1 May 9, 2002

Related U.S. Application Data

(60) Continuation of application No. 09/688,619, filed on Oct. 16, 2000, now Pat. No. 6,541,261, which is a division of application No. 09/032,676, filed on Feb. 27, 1998, now Pat. No. 6,183,693.

(51) Int. Cl.[7] .............................................. G01N 1/31
(52) U.S. Cl. ............................................ 422/64; 422/67
(58) Field of Search ............................ 422/64, 67, 104; 436/43, 46; 219/385, 386, 389, 521, 477, 478, 480

(56) References Cited

U.S. PATENT DOCUMENTS

| | | | |
|---|---|---|---|
| 3,853,092 A | 12/1974 | Amos et al. | 118/56 |
| 3,979,576 A | 9/1976 | Janson | 219/489 |
| 4,043,292 A | 8/1977 | Rogers et al. | 118/5 |
| 4,092,952 A | 6/1978 | Wilkie et al. | 118/58 |
| 4,296,069 A | 10/1981 | Smith et al. | 422/64 |
| 4,358,470 A | 11/1982 | Rasmussen | 427/4 |
| 4,384,193 A | 5/1983 | Kledzik et al. | 219/521 |
| 4,430,299 A | 2/1984 | Horne | 422/64 |
| 4,543,236 A | 9/1985 | von Gise | 422/50 |
| 4,629,862 A | 12/1986 | Kitagawa et al. | 219/200 |
| 4,731,335 A | 3/1988 | Brigati | 436/180 |
| 4,847,208 A | 7/1989 | Bogen | 436/174 |
| 4,858,155 A | 8/1989 | Okawa et al. | 364/557 |
| 4,865,986 A | 9/1989 | Coy et al. | 435/290 |
| 4,933,146 A | 6/1990 | Meyer et al. | 422/63 |
| 4,985,206 A | 1/1991 | Bowman et al. | 422/99 |
| 5,073,504 A | 12/1991 | Bogen | 436/174 |
| 5,075,079 A | 12/1991 | Kerr et al. | 422/64 |
| 5,105,066 A | 4/1992 | Houdy et al. | 219/385 |

(List continued on next page.)

FOREIGN PATENT DOCUMENTS

| | | |
|---|---|---|
| EP | 0 201 780 | 11/1986 |
| WO | WO 93/09486 | 5/1993 |

OTHER PUBLICATIONS

Stross, W.P., et al., "Automation of APAAP Immunocytochemical Technique," J. Clin. Pathol., 42:106–112 (1989).

Stark, E., et al., "An Automated Device for Immunocytochemistry," Journal of Immunological Methods, 107:89–92 (1988).

MaWhinney, W.H.B., et al., "Automated Immunochemistry," J. Clin. Pathol., 43(7): 591–596 (1990).

*Primary Examiner*—Jeffrey R. Snay
(74) *Attorney, Agent, or Firm*—Hamilton, Brook, Smith & Reynolds, P.C.

(57) ABSTRACT

An automated slide stainer with slides mounted in a horizontal position on a rotary carousel. Reagents and rinse liquids are automatically dispensed onto tissue sections or cells mounted on slides for the purpose of performing chemical or immunohistochemical stains. The rinse liquids are removed by an aspiration head connected to a source of vacuum. Individual slides or groups of slides are supported on flat heating stations for heating to individual temperatures. Temperature control electronics on the carousel are controlled by a user interface off of the carousel.

13 Claims, 20 Drawing Sheets

U.S. PATENT DOCUMENTS

| | | | |
|---|---|---|---|
| 5,154,889 A | 10/1992 | Muraishi | 422/65 |
| 5,207,987 A | 5/1993 | Kureshy et al. | 422/67 |
| 5,231,029 A | 7/1993 | Wootton et al. | 435/289 |
| 5,246,665 A | 9/1993 | Tyranski et al. | 422/64 |
| 5,273,905 A | 12/1993 | Muller et al. | 435/301 |
| 5,280,156 A | 1/1994 | Niori et al. | 219/385 |
| 5,316,452 A | 5/1994 | Bogen et al. | 417/412 |
| 5,425,918 A | 6/1995 | Healey et al. | 422/64 |
| 5,439,649 A | 8/1995 | Tseung et al. | 422/99 |
| 5,475,610 A | 12/1995 | Atwood et al. | 364/500 |
| 5,496,518 A | 3/1996 | Arai et al. | 422/64 |
| 5,523,056 A | 6/1996 | Miller | 422/64 |
| 5,595,707 A | 1/1997 | Copeland et al. | 422/64 |
| 5,601,141 A | 2/1997 | Gordon et al. | 165/263 |
| 5,645,114 A | 7/1997 | Bogen et al. | 141/145 |
| 5,819,842 A | 10/1998 | Potter et al. | 165/206 |
| 6,296,809 B1 | 10/2001 | Richards et al. | 422/64 |

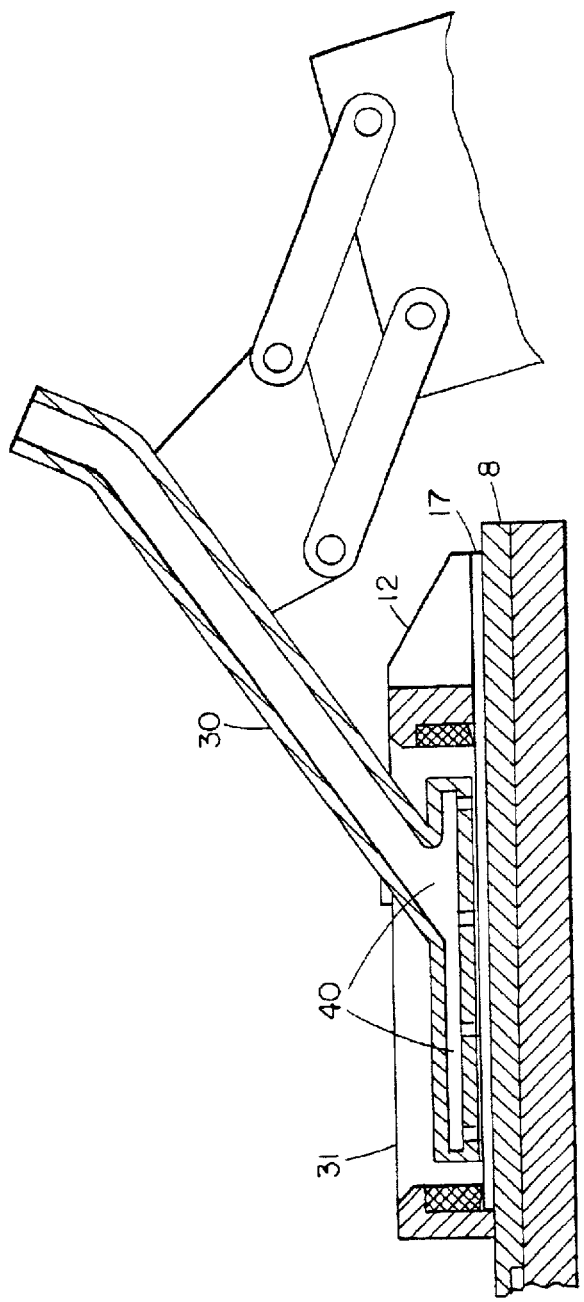
FIG. IIA
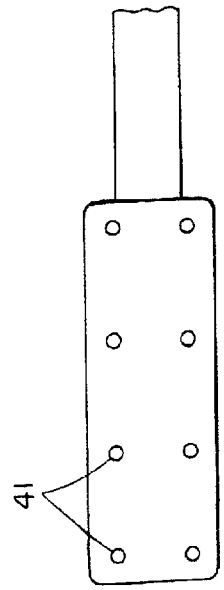
FIG. IIB

RANDOM ACCESS SLIDE STAINER WITH INDEPENDENT SLIDE HEATING REGULATION

RELATED APPLICATIONS

This application is a continuation of U.S. application Ser. No. 09/688,619, filed Oct. 16, 2000, now U.S. Pat. No. 6,541,261, which is a divisional application of U.S. application Ser. No. 09/032,676, filed Feb. 27, 1998, now U.S. Pat. No. 6,183,693. The entire teachings of the above applications are incorporated herein by reference.

BACKGROUND OF THE INVENTION

Tissue sections or cellular monolayers are commonly examined by microscopic examination, for both research and clinical diagnostic purposes. Thin tissue sections or cellular preparations are commonly 1–10 microns thick, and are nearly transparent if untreated. In order to visualize various histologic features, a wide array of staining procedures have been developed over the years that highlight various cellular or extracellular components of the tissues. Histochemical stains, also commonly termed "special stains," employ chemical reactions to color various chemical moieties. Immunohistochemical stains employ antibodies as probes to color specific proteins, commonly via enzymatic deposition of a colored precipitate. Each of these histochemical and immunohistochemical stains requires the addition and removal of reagents in a defined sequence for specific time periods, at defined temperatures. Therefore, a need arises for a slide stainer that can perform a diversity of stains simultaneously under computer control, as specified by the technologist.

An early slide stainer for immunohistochemistry was described by David Brigati M. D., U.S. Pat. No. 4,731,335. In that disclosure, microscope slides were closely apposed to each other, to form capillary gaps. The pairs of slides were mounted in a holder that could be moved about by a mechanical arm along three axes. If slides were to be heated, all of the slides were moved as a group into a humidified heated chamber. Therefore, random access capability is not possible with this design.

In another slide stainer by Rogers and Sullivan, U.S. Pat. No. 4,043,292, slides are mounted on a rotary carousel. Their invention heats the slides by passing a heated stream of air over the slides. All of the slides are heated to the same temperature.

Wooton, McLeod, and Read disclose another slide stainer that incorporates heat capability, in U.S. Pat. No. 5,231,029. In that invention, a steam chamber is provided to heat slides. The humidity in the steam chamber is designed to be just below 100 percent. If the slides are to be heated, they are placed into the chamber. Since the slides are either in or out of the chamber, all slides must be brought to the same heated temperature, a temperature approximately that of steam (100° C.).

A recently described batch slide stainer commercialized by Ventana Medical Systems, Inc. is disclosed in U.S. Pat. No. 5,595,707 by Copeland, et. al. In that disclosure, slides are placed on a rotary carousel that allows for the addition and flushing of reagents from the slide surface. Their slide stainer includes a heating chamber that is heated by the introduction of warm air. A temperature sensor is contained within the chamber for providing temperature feedback to a microprocessor. Similar to the other slide stainers described above, all slides must be brought to the same temperature.

SUMMARY OF THE INVENTION

This invention relates to an improved slide staining device, for the application and removal of reagents to biologic tissue sections mounted on microscope slides. The improvement relates to the random access capability of the slide stainer, i.e., one that performs any of a list of procedures to any of a plurality of biologic samples mounted on microscope slides. Since various procedures require heat at different times to enhance the rate of chemical reaction, a means has been developed to heat slides to different temperatures, independently of the temperatures of other slides. This invention allows for heating each slide to its own specified temperature.

Any of the previously-described systems could potentially be modified to duplicate their heater control systems to provide for multiple levels of heating control. For example, commercial thermal cyclers are now available that incorporate four different heating blocks that share the same microprocessor. However, the type of hard-wired temperature control mechanism that heats and cools four different blocks would be expensive and cumbersome as the number of independent samples increases. For example, in the preferred embodiment of the present invention, forty-nine independent heating positions are described. If we assume that two wires provide power to the heater, and two wires provide temperature feedback from each heating sensor, then a total of 196 wires would need to be connected between the different heaters and the computer control circuitry. Placing all of these wires on a service loop between a stationary computer and a moving slide stainer presents yet another difficulty, increasing the cost of manufacture and servicing.

In accordance with one aspect of the invention, a moving plating, preferably a carousel, is adapted to support a plurality of microscope slides bearing biological samples. In particular, a plurality of flat heating stations are provided on the platform, each heating station supporting at least one microscope slide and, in a preferred embodiment, each heating surface supporting a single microscope slide. The heating stations are individually controlled to control temperatures to which the slides are heated.

According to another aspect of the invention, a plurality of heaters that can each heat at least one slide are associated with a moving platform that is adapted to support a plurality of microscope slides. Each heater includes a heating element set, each set having at least one heating element. A temperature controller electronic circuit mounted on the moving platform provides electrical power to the heating element such that each heating element set can be heated to a different temperature. A user interface mounted off of the moving platform specifies the desired temperatures for the microscope slides through a communication link with the temperature controller electronic circuit.

Preferably, the communication link is a group of wires, the number of wires being fewer than the number of heating elements. To that end, the temperature controller electronic circuit may include a shift register which receives control data from the user interface, multiple shift registers of plural controllers being daisy chained. Individual temperature sensors may also be provided to provide temperature feedback information to the temperature controller electronic circuit.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 11A is a side cross-sectional view of the aspiration head, showing its relationship to the glass slide in the slide frame.

FIG. 11B is a bottom en face view of the aspiration head.

DETAILED DESCRIPTION OF THE INVENTION

Figure 1:
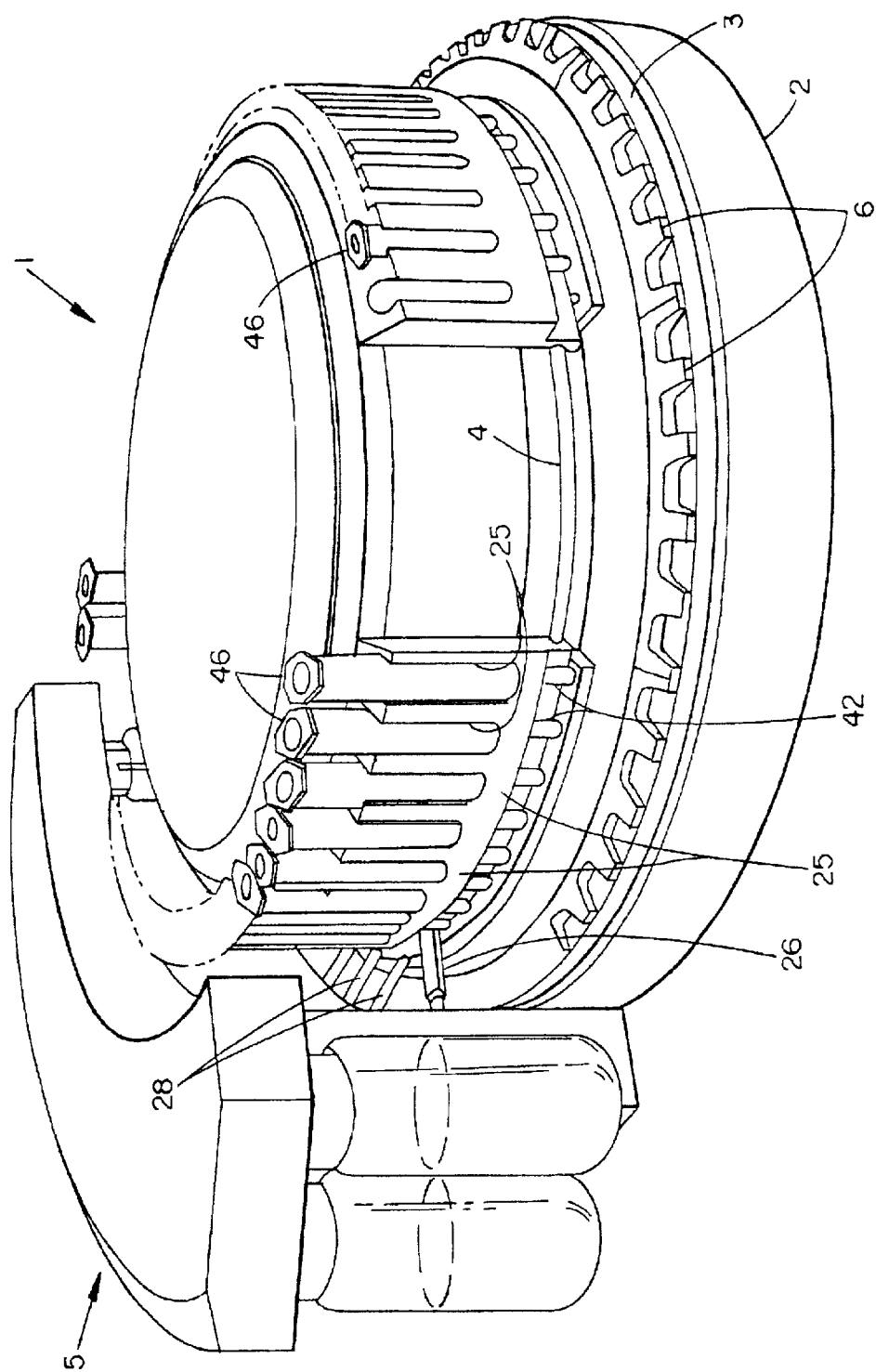
FIG. 1 is a perspective view of a first embodiment of a slide stainer.

FIG. 1 shows a first embodiment 1 of the invention in perspective view. Generally, the first embodiment 1 comprises a substantially circular assembly base 2, a slide rotor 3 rotatable on the assembly base 2, a reagent rotor 4 also rotatable on the assembly base, and a liquid dispensing and removal station 5.

Figure 2:
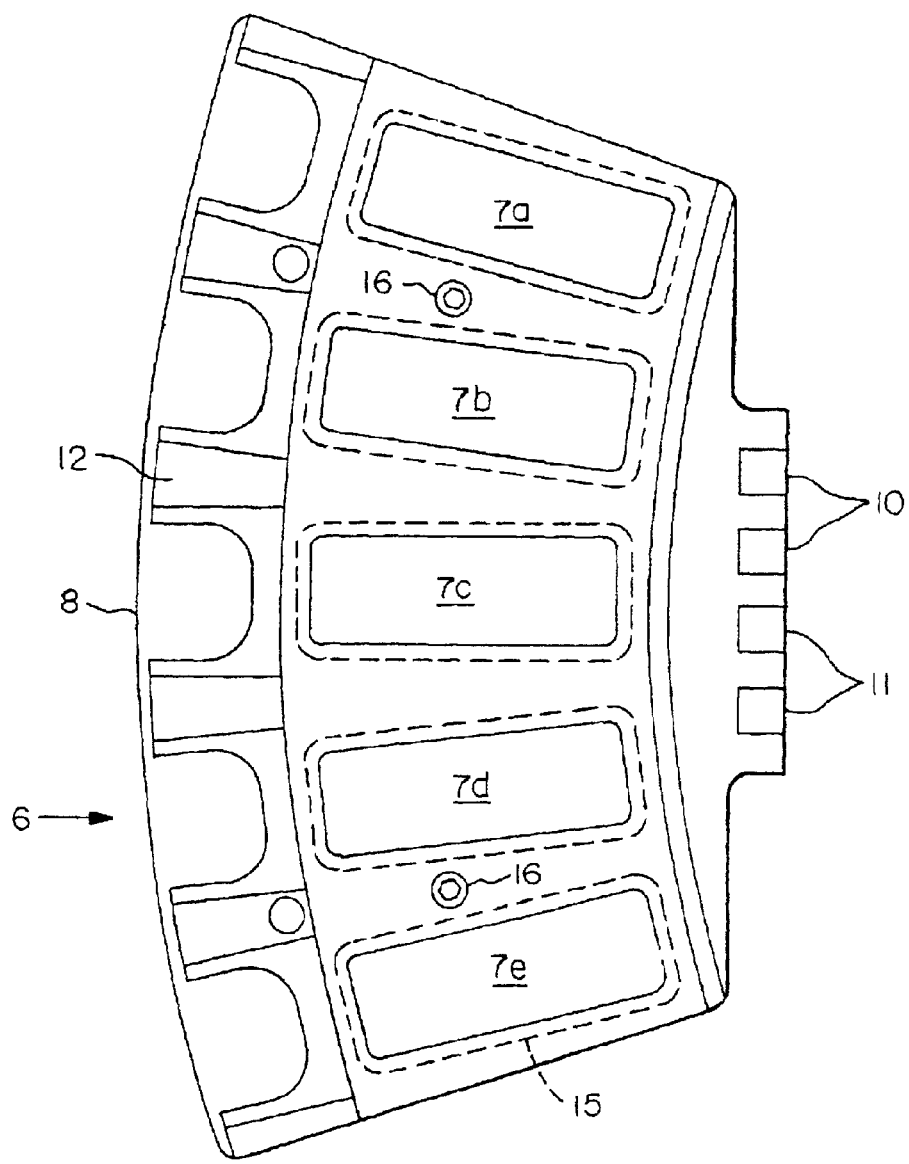
FIG. 2 is a top view of a slide frame for providing five sealed cavities above five different slides holding tissue samples.

The slide rotor 3 is driven to rotate by a servo motor (not shown) and carries ten slide frames 6 that are radially asserted into and detachable from it. A top view of single slide frame 6 is shown in FIG. 2. Here, positions for five slides, each with a tissue sample, are shown in positions 7a–7e. The slide frame 6 comprises a slide frame base 8 shown in FIG. 3. The slide frame base 8 includes a heated area 9 which underlies each of the slide positions 7a–7e and incorporates resistive heating elements, not shown. The heating elements are integrally formed in the slide frame base 8. Electricity for powering the heating elements is provided into the slide frame 6 from the assembly base 2 via first and second contacts 10. Further, third and fourth contacts 11 enable temperature sensing of the heated areas via thermocouples also integrally formed in the slide frame base 8. In practice, a sum of three connectors are required, since contacts 10 and 11 share the same ground connection. Therefore, one of the connectors 11 are left unused.

Figure 4:
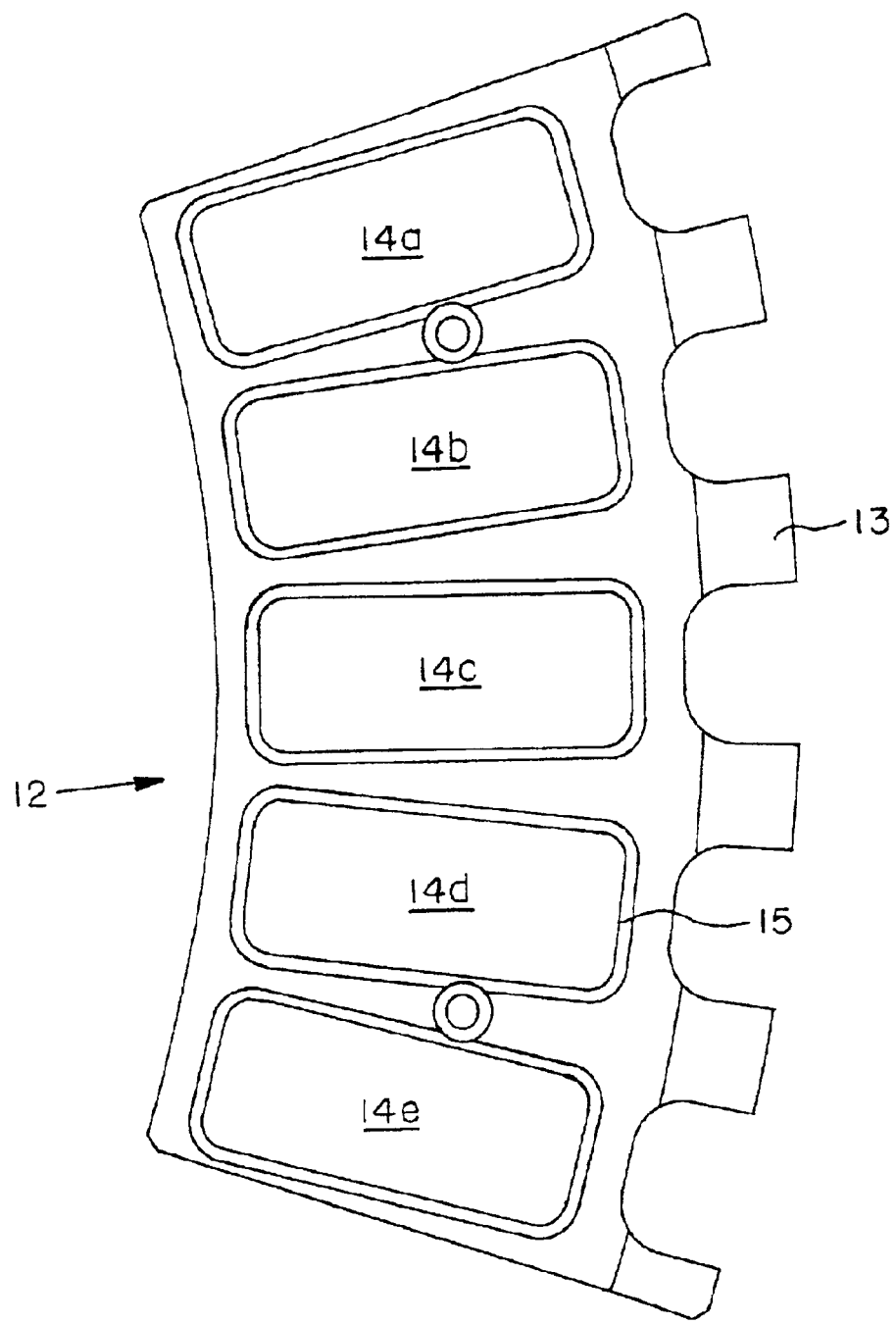
FIG. 4 is a bottom view of a slide frame housing.

Adapted to overlay the slide frame base is a slide frame housing 12. FIG. 4 is a top view of the slide frame housing 12 showing essentially a rigid plastic or metal frame 13 with five oval holes 14a–14e corresponding to each of the slide positions 7a–7e. A silicon rubber gasket 15 is also provided under the frame 13. Returning to FIG. 2, the slide frame housing 12, including the gasket 15 and frame 13, is bolted onto the slide frame base 8 by two Allen bolts 16 to provide individual sealed cavities approximately 0.2–0.4 inches deep over each tissue sample slide placed at each of the slide positions 7a–7e. As a result, a total of 3 ml of reagents and/or rinses can be placed in contact with the tissue samples of each one of the slides but a maximum quantity of 2 ml is preferable. Since the silicon gasket 15 is compressed by the frame 13 against the microscope slides (not shown), the cavities over each of the frame positions are mutually sealed from each other.

Figure 3:
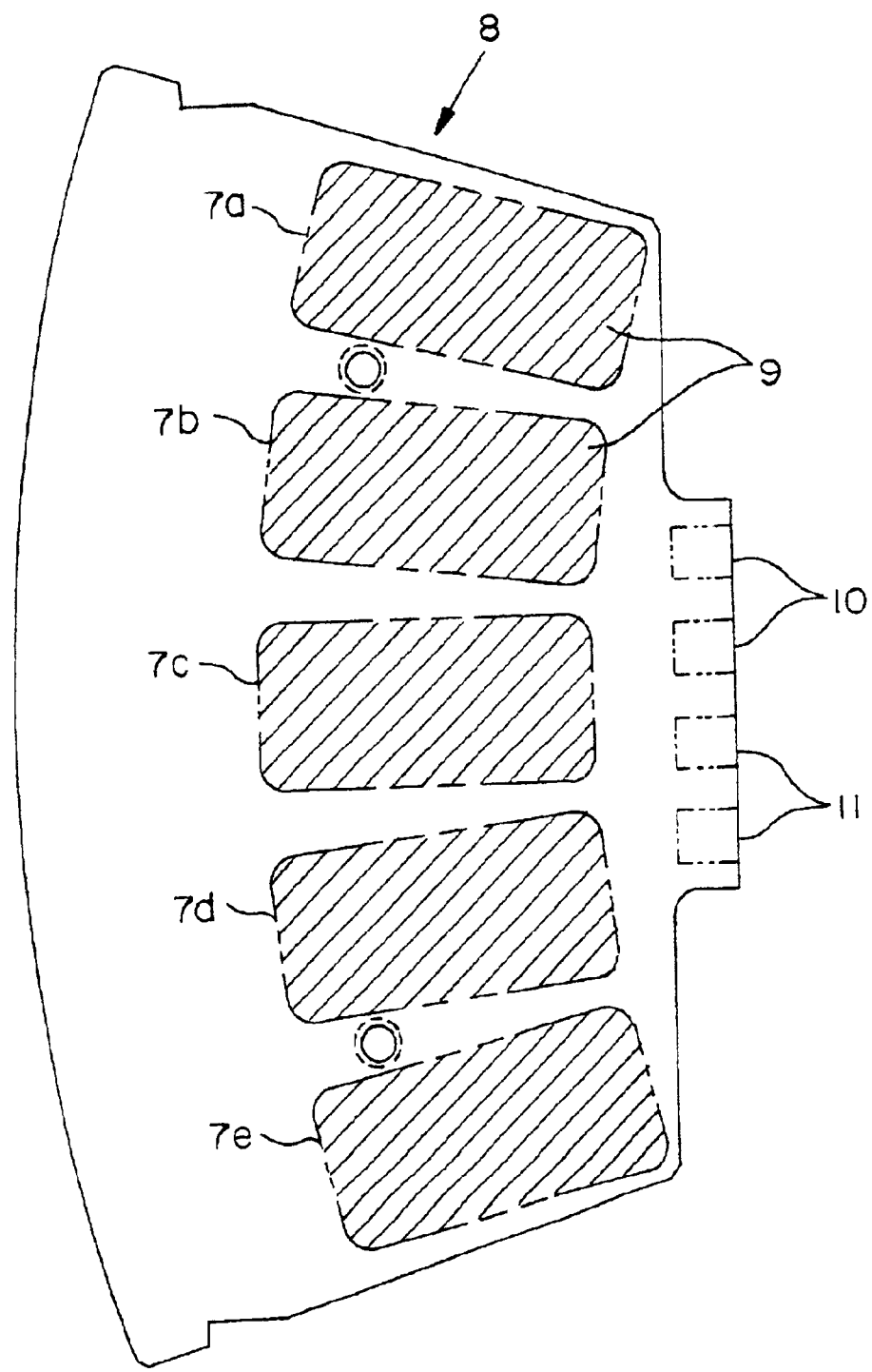
FIG. 3 is a top view of a slide frame base.
Figure 5:
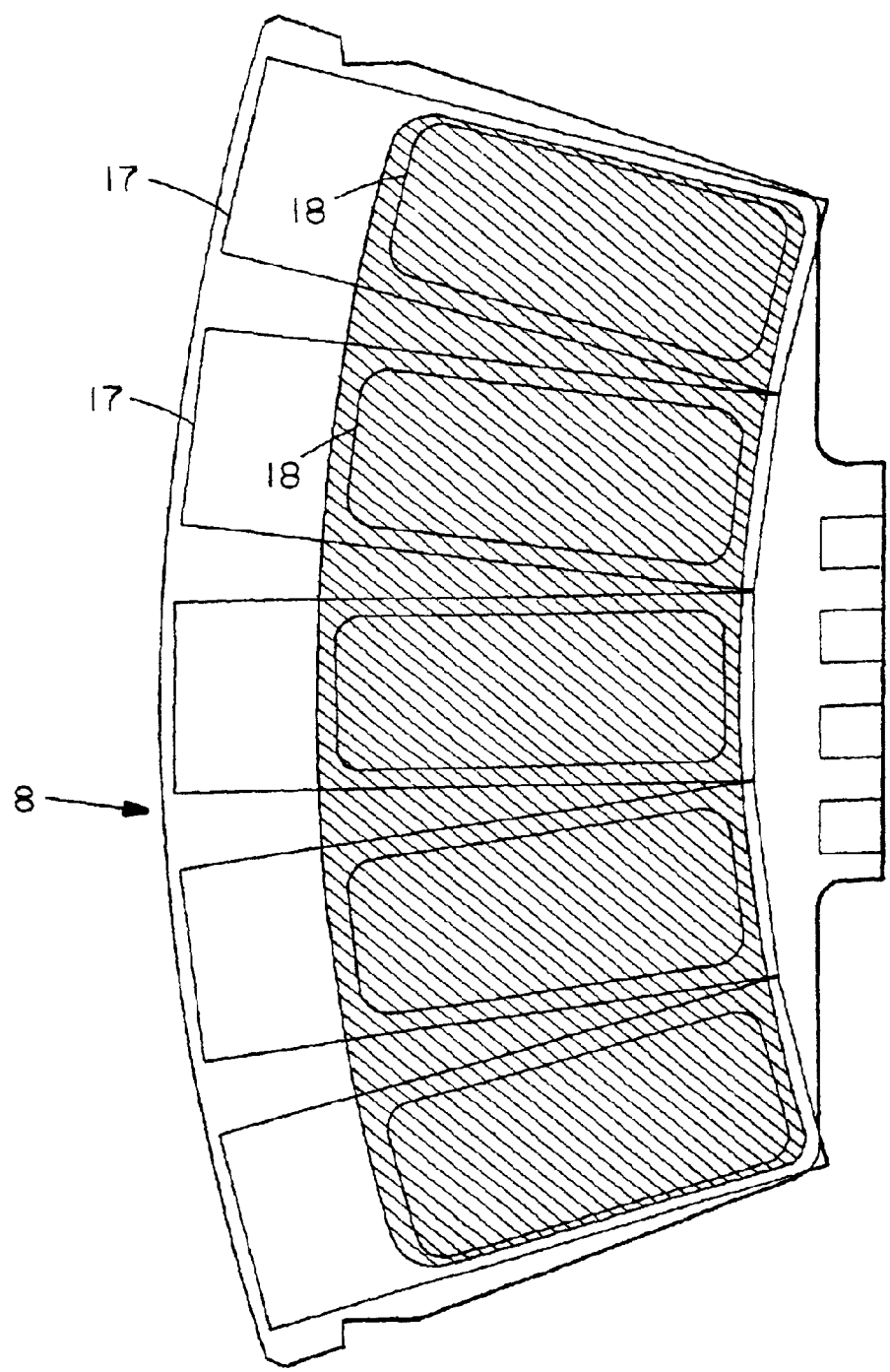
FIG. 5 is a top view of the slide frame housing with five microscope slides in their appropriate positions, showing the area to which heat is applied.

FIG. 5 is a top view of a slide frame base 8 with five microscope slides 17 in the positions denoted by 7a–7e in FIG. 3. The area of each slide 17 forming cavities, that are delimited by the silicone rubber gasket 15 and holes 14a–14e is indicated by an approximately rectangular line 18, marking the chamber wall. The area denoted by the hatched bars indicates the area of the slide frame base 8 that includes heating elements 9. The entire heated area (hatched bars) is raised to the same temperature, bringing the group of five slides to the same desired temperature. The portion of each slide 17 that is not above the heated area does not generally bear a biologic tissue specimen. Rather, it is used for labeling purposes.

Figure 6:
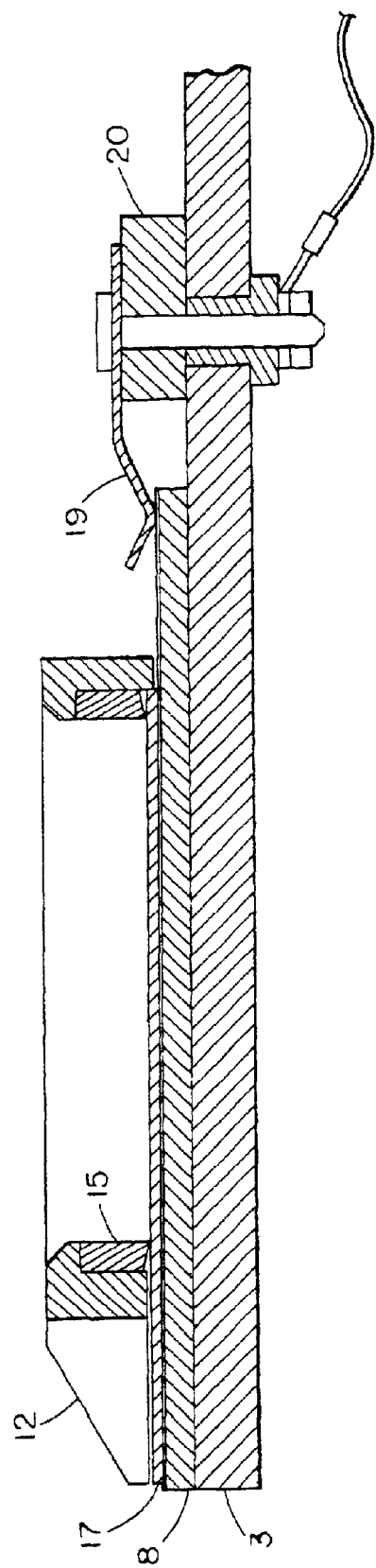
FIG. 6 is a cross-sectional view of a slide frame resting on the slide rotor.

FIG. 6 is a cross-sectional view of an assembled slide frame base 8 and housing 12, collectively referred to previously as the slide frame 6. The microscope slide 17 is shown held in position, between the slide frame base 8 and housing 12. The slide frame 6 is resting on the slide rotor 3. In this view, the electrical connection between the slide frame 6 and an edge connector 19 is demonstrated. Four edge connectors per slide frame 6 are provided (contacts 10 and 11 in FIGS. 2 and 3). The electrical connection is fed from the edge connector 19 through the slide rotor via an insulated feed-through 20, to a terminal underneath the slide rotor 3. A wire then connects the terminal to a source of power or control circuitry (not shown).

Figure 7:
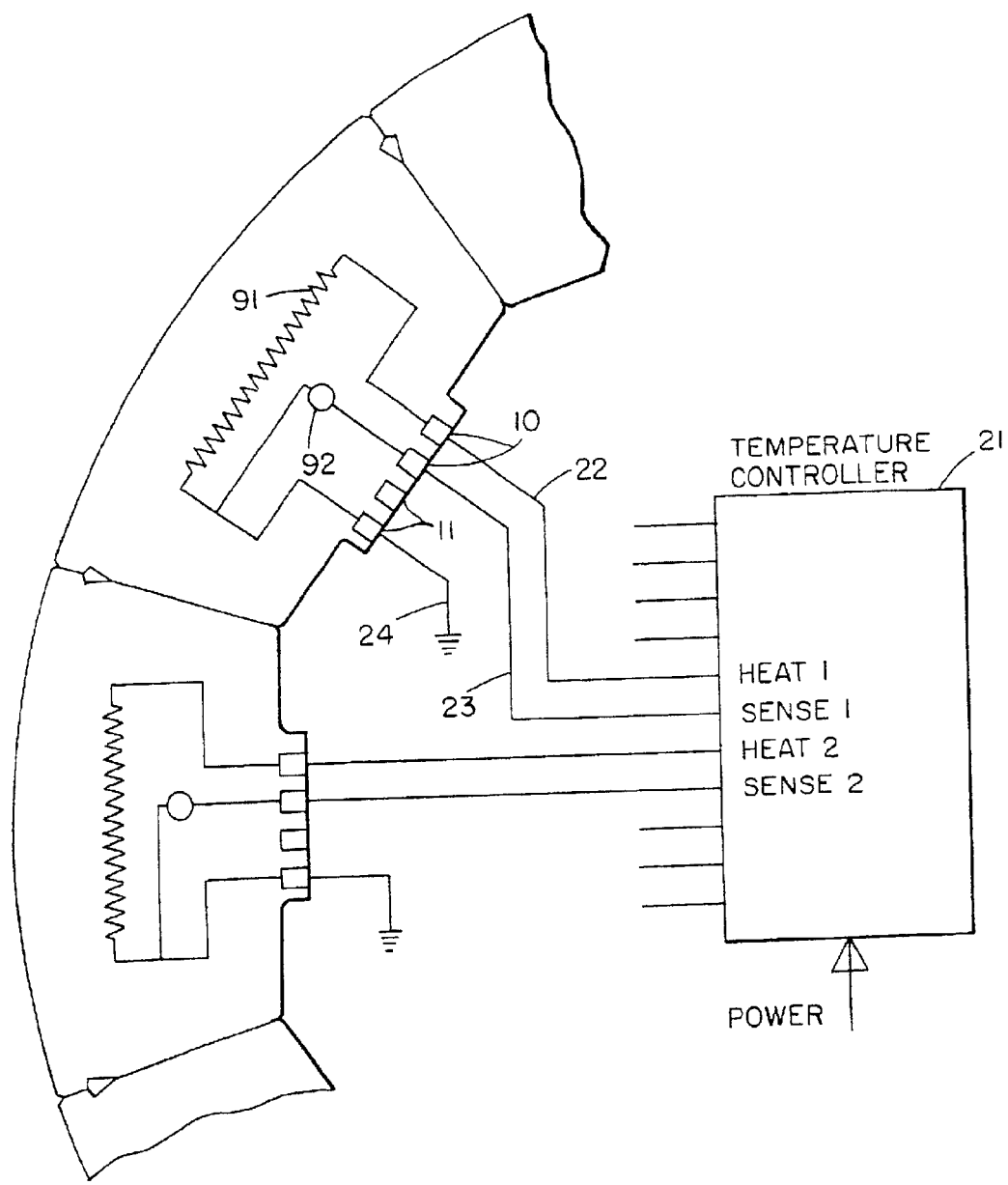
FIG. 7 is a schematic diagram of the heater and sensor wiring diagram, on the slide frame, and the interconnection with the temperature controller.

FIG. 7 is a schematic diagram, showing two out of the ten heater 91 and sensor 92 circuits that can be placed on the instrument slide rotor. The heater is represented schematically as a resistive element, and corresponds to the heated area (hatched bars) of FIG. 5. Contacts 10 and 11 share a common ground connection, leaving one of the four connectors unused. Each of the circuits feeds into a temperature controller, represented schematically 21. Each slide frame sends three wires to the temperature controller 21—a heater power conductor 22, a sensor conductor 23, and a ground connection 24. The temperature controller 21 is mounted in a stationary position on the assembly base 2. Since the heaters and sensors are in frequent motion, they connect to the stationary temperature controller 21 via a service loop (not shown). The service loop contains the wires from each of the edge connectors 19. Sufficient extra length is provided in the wires so that as the slide rotor rotates, the service loop travels around the slide rotor axis. The slide rotor 3 does not turn more than one full revolution in either direction. The wires in the service loop are preferably bundled together with a wire tie, so that individual wires do not become entangled or caught underneath the slide rotor 3. Since there are three wires per circuit (wires 22–24), and there are ten slide frames 6 on the slide rotor 3, the service loop contains a minimum of thirty wires.

Referring to FIG. 1, positioned above the slide rotor 3 is the reagent rotor 4. This reagent rotor is similarly adapted to rotate on the assembly base 2 and is driven by another servo motor (not shown) under computer control (not shown). The reagent rotor 4 and the slide rotor 3 rotate independently of each other. The reagent rotor 4 is adapted to carry up to ten cartridge frames 25. Each of these cartridge frames 25 are detachable from the reagent rotor 4 and can be selectively attached at any one of ten possible points of connection. Each cartridge frame 25 is capable of carrying five of the cartridge pumps 46.

Figure 8:
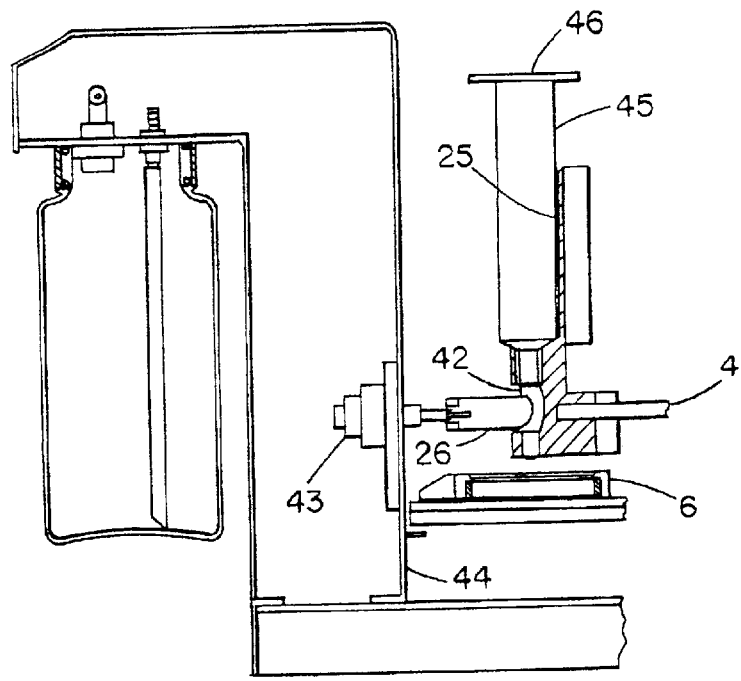
FIG. 8 is a side cross-sectional view of a cartridge pump dispensing mechanism in the liquid dispensing and removal station.

Generally, the dispensing station 5 comprises a soft hammer 26 for engaging a portion of the cartridge pumps 46. The cartridge pumps 46 are constructed so as to dispense liquid when a portion of the cartridge pump 46, called the metering chamber 42 of the cartridge pump 46 is compressed. It is possible to dispense from any of a plurality of cartridge pumps by rotating the reagent rotor so as to align a desired cartridge pump 46 with the hammer 26. This provides the capability of dispensing precisely measured amounts of reagent to any slide positioned underneath the cartridge pump 46 adjacent to actuator 26. The mechanism for dispensing from the cartridge pumps 46 is shown in greater detail in FIG. 8. The hammer 26 is driven by a solenoid or linear stepping motor 43 that is mounted on a front wall 44, attached to the assembly base 2. In FIG. 8, the hammer is shown compressing the metering chamber 42 portion of the cartridge pump. It is important to be able to adjust the speed of compression by the hammer 26 upon the metering chamber 42. Otherwise, too rapid a compression will cause an excessively forceful ejection of reagent from metering chamber 42, potentially damaging the tissue section underneath. Therefore, a linear stepping motor is preferred instead of a solenoid. As another alternative, the reciprocating hammer of the dispensing actuator could take the form of a cam, driven by a rotary motor, that engages the metering chamber 42 so that the rotation of the cam will compress the metering chamber.

The cartridge pump 46 is comprised of a liquid reservoir 45 and the metering chamber 42. The liquid reservoir 45 shown in this first embodiment 1 is a syringe barrel. The metering chamber 42 is comprised of a compressible elastomeric housing with a one-way inlet valve (not shown) and a one-way outlet valve (not shown), both valves aligned in a downwards direction of fluid flow. When the hammer 26 compresses the metering chamber 42, the liquid reagent contained within is ejected. When the compressive force is removed, the negative pressure created by the expansion of the elastomeric housing, trying to resume its native, non-compressed shape, causes liquid to flow inwards from the liquid reservoir 45. In this manner, repetitive compression of the metering chamber 42 causes repetitive dispensing of small aliquots of reagent. Alternative cartridge pumps are presented in U.S. patent application Ser. No. 08/887,178 filed Jul. 2, 1997 and U.S. patent application Ser. No. 09/020,983 filed Feb. 10, 1998 which are incorporated herein by reference.

Figure 9:
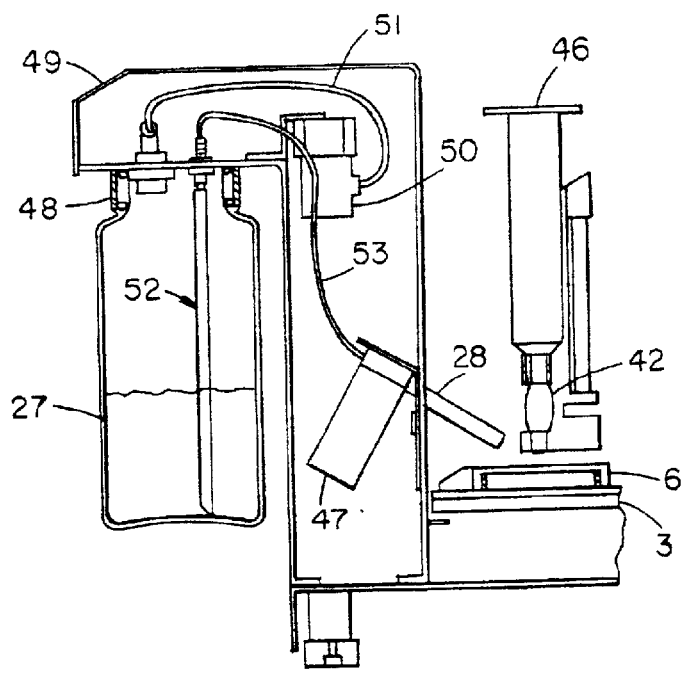
FIG. 9 is a side cross-sectional view of a bulk liquid dispensing station housed in the liquid dispensing and removal station.

The dispensing station 5 further includes a means to dispense liquids from a large bottle (FIG. 9). Bulk liquid bottles 27 that can supply liquid into any one of the microscope slides 17 on any one of the slide frames 6 via rinse tubes 28. Each bulk liquid bottle 27 is connected to its own rinse tube 28. The bulk liquid bottles 27 are pressurized by a pump (not shown). The outflow tube (not shown) from each bulk liquid bottle 27 passes through a valve 47 that regulates the flow of liquid from that bottle. By opening the valve for a defined period of time, under computer control (not shown), with a defined pressure within the bottle 27, a known quantity of liquid can be dispensed onto the slide 17. The liquids placed within the bottles 27 are those that are used repeatedly among many different procedures, such as water, saline, and alcohol.

As shown in FIG. 9, the bulk liquid bottles 27 are screwed into a female threaded cap 48 secured to the underside of the horizontal top wall 49 of the station frame. Compressed air from a compressor (not shown) is provided to each bulk liquid bottle 27 through a pressure regulator 50. Tubing from the pressure regulator 51 transmits the compressed air to the inlet of the bulk liquid bottle 27. The pressure above the liquid enables the liquid to forced up through the dip tube 52 through the rinse hose 53 when a pinch valve 47 is opened. Depending on the length of time that the pinch valve is opened, a pre-determined amount of liquid can be dispensed through the rinse tube 28.

Figure 10A:
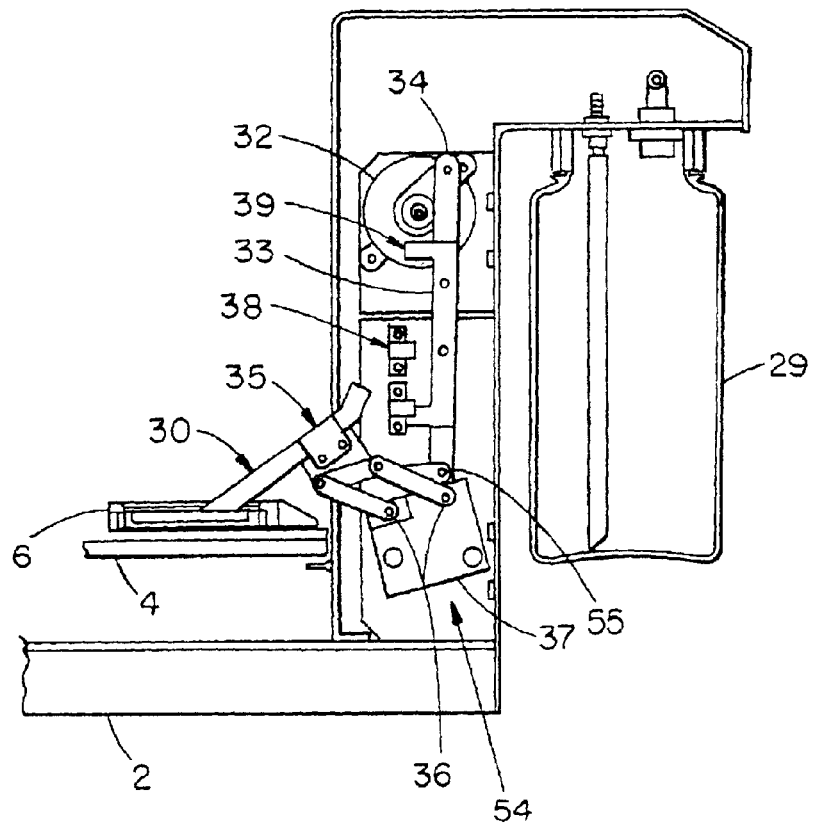
FIGS. 10A and 10B are side cross sectional views of a vacuum hose and transport mechanism for removing liquid reagent and wash fluids from slides contained on the slide rotor.
Figure 10B:
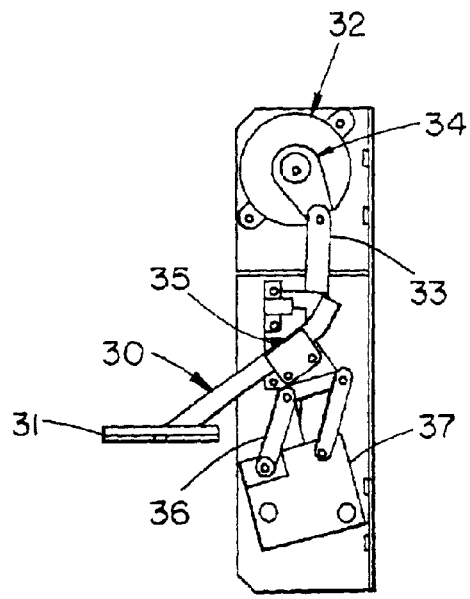

The liquid dispensing and removal assembly 5 further includes a liquid removal vacuum station, positioned adjacent to the rinse tubes 28 (not visible in FIG. 1). In order to remove liquid from the surface of a slide 17, the reagent rotor positions the slide at the liquid removal vacuum station, shown in a side cross-sectional representation in FIGS. 10A and 10B. An external source of vacuum (not shown) is channeled through a trap flask 29, ultimately leading to a vacuum hose 30 that terminates in an aspiration head 31. The tubing connections are not shown in FIGS. 10A and 10B. The vacuum hose 30 and aspiration head 31 are supported by a hose transport mechanism 54 that allows the aspiration head 31 to be extended down into a cavity of a slide frame 6 to remove liquid covering the tissue sample on the slide 17. As the aspiration head contacts the liquid, the liquid is sucked upwards into the tubing and collected into the trap flask 29.

The vacuum hose transport mechanism 54 comprises a motor 32. A reciprocating link 33 is attached to a crank arm 34 so that the rotation of the motor 32 causes the reciprocating link 33 to traverse in a vertical direction. A bottom portion of the reciprocating link 33 is connected to a lever 55 that is pivotally attached to the station frame. The other end of this lever is connected to a vacuum hose clamp 35 that is connected via pivot arms 36 to a plate 37 rigidly attached to the station frame. The net effect of these connections is that when the motor 32 is rotated, the slide arm 33 descends in a vertical direction. Thus, the lever 55 is pivoted clockwise around its fulcrum causing the hose clamp 35 to pivot up and away on the two pivot arms 36 from the slide as shown in FIG. 1013. The motor is automatically turned off as the link 33 reaches its two extreme ends of movement by the contact of the electrical terminals 39 of the link to the contact plates 38 connected to the station frame.

The aspiration head 31 is shown in greater detail in FIGS. 11A and 11B. FIG. 11A shows the aspiration head in a lowered position, in cross-section, within the cavity formed by the slide frame 6. The aspiration head 31 comprises a hollow interior manifold 40 through which the vacuum force is transmitted across the entire lower surface of the aspiration head 31. Eight holes 41 are drilled on the lower face of the aspiration head 31, through which the suction force is transmitted. Since the microscope slide 17 is planar, liquid on the slide surface spreads out in two dimensions. Therefore, in order to thoroughly remove liquid from all portions of the microscope slide 17, multiple aspiration sites are needed. We accomplish this with an aspiration head with a planar lower surface with multiple holes. The planar surface of the aspiration head 31 comes into close parallel apposition to the microscope slide 17. The aspiration head only contacts the liquid, not the microscope slide itself, lest it damage the glass slide 17 or the biologic specimen that it carries (not shown). Without such a design and only a single aspiration site, such as from a pipette, liquid distant from the aspirator would not be removed. Rather, it would cling to the distant surfaces of the glass slide 17, because of the surface tension on the glass. This would result in a residual volume of liquid that would otherwise be left on the surface of the slide 17. Having a close parallel apposition of the aspiration head is also helpful from the perspective of decreasing surface tension during liquid aspiration. The close parallel apposition of the bottom surface of the aspiration head with the microscope slide 17 creates a type of capillary gap. This gap helps to overcome surface tension, ensuring complete liquid removal.

A computer, not shown, controls the instrument functions. That is, an operator programs the computer with the information such as the location of reagents on the reagent rotor and the location of slides on the slide rotor. The operator then programs the particular histochemical protocol to be performed on the tissue samples. Variables in these protocols can include the particular reagent used on the tissue sample, the time that the tissue sample is allowed to react with the reagent, whether the tissue sample is then heated, the rinse that is then used to wash the reagent away, followed by the subsequent removal of the rinse and reagent to allow subsequent exposure to a possibly different reagent. The instrument enables complete random access, i.e., any reagent to any slide in any sequence.

Figure 12:
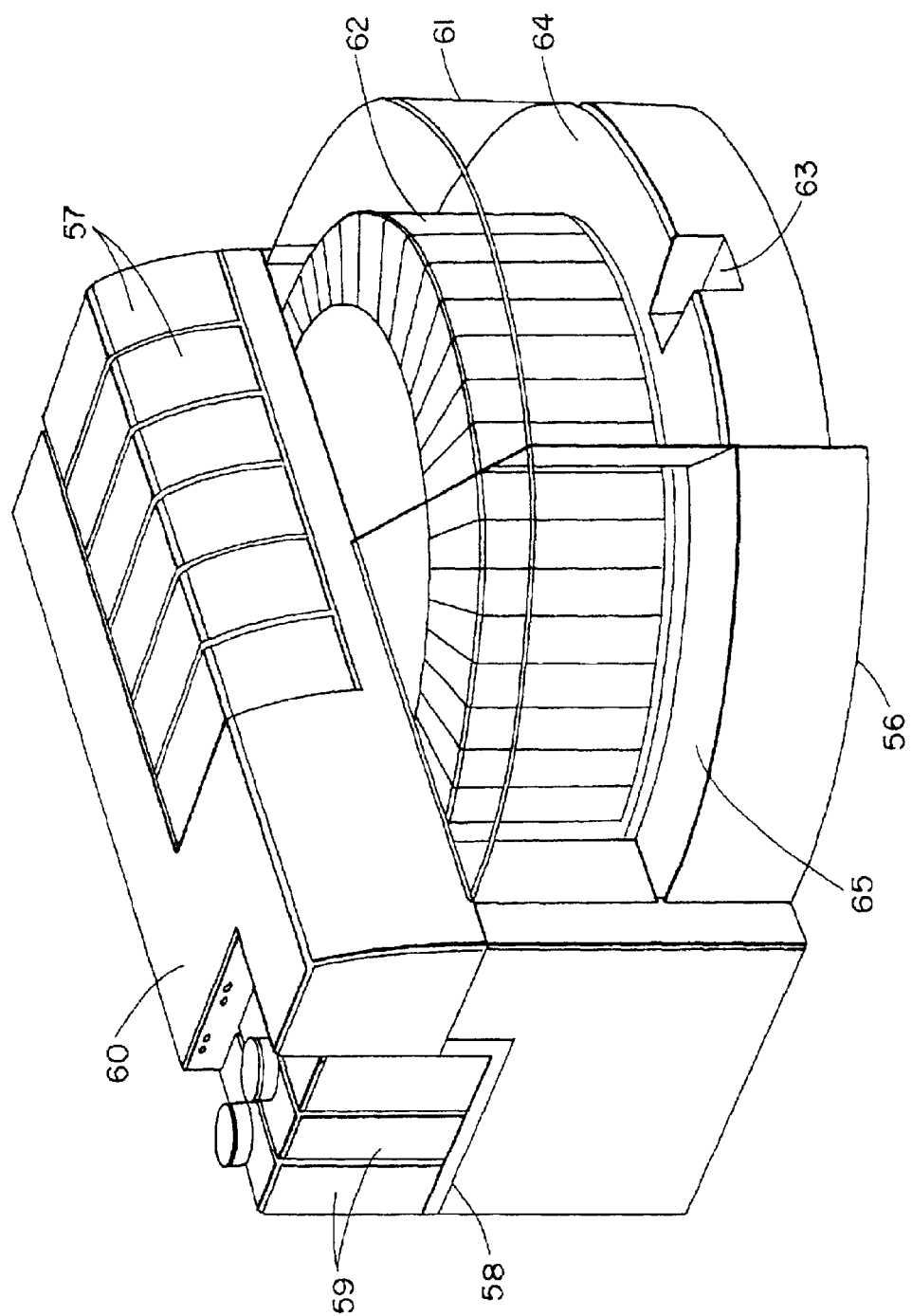
FIG. 12 is a perspective view of a second embodiment of a slide stainer.

A second, preferred, embodiment of the invention is shown in FIG. 12. Like the previous embodiment, it also comprises two independent carousels that rotate on an assembly base 56. Bulk liquid bottles 57 are mounted on a bridge 58 that extends across the width of the entire machine, above the reagent rotor. A separate group of trap bottles 59, for collecting waste liquid, are mounted on the side of the bridge 58 in a compartmentalized shelf. The tubing connections and valves for the bulk liquid bottles 57 and the trap bottles 59 are hidden from view by an upper panel 60. The front and sides of this embodiment are surrounded by a plexiglass case 61, that can be manually slid sideways in order to insert cartridge pumps 62 or slides (not shown). Slides are individually inserted and removed via a centrally located slide access door 63. The slides (not shown) are hidden from view by a circular platen 64 that is located above the slides and reagent rotor (not shown). Functions similar to the dispensing assembly (5 of FIG. 1) in the previous embodiment are accomplished in a somewhat similar liquid handling assembly (not shown) that is positioned in a liquid handling zone 65.

Figure 13:
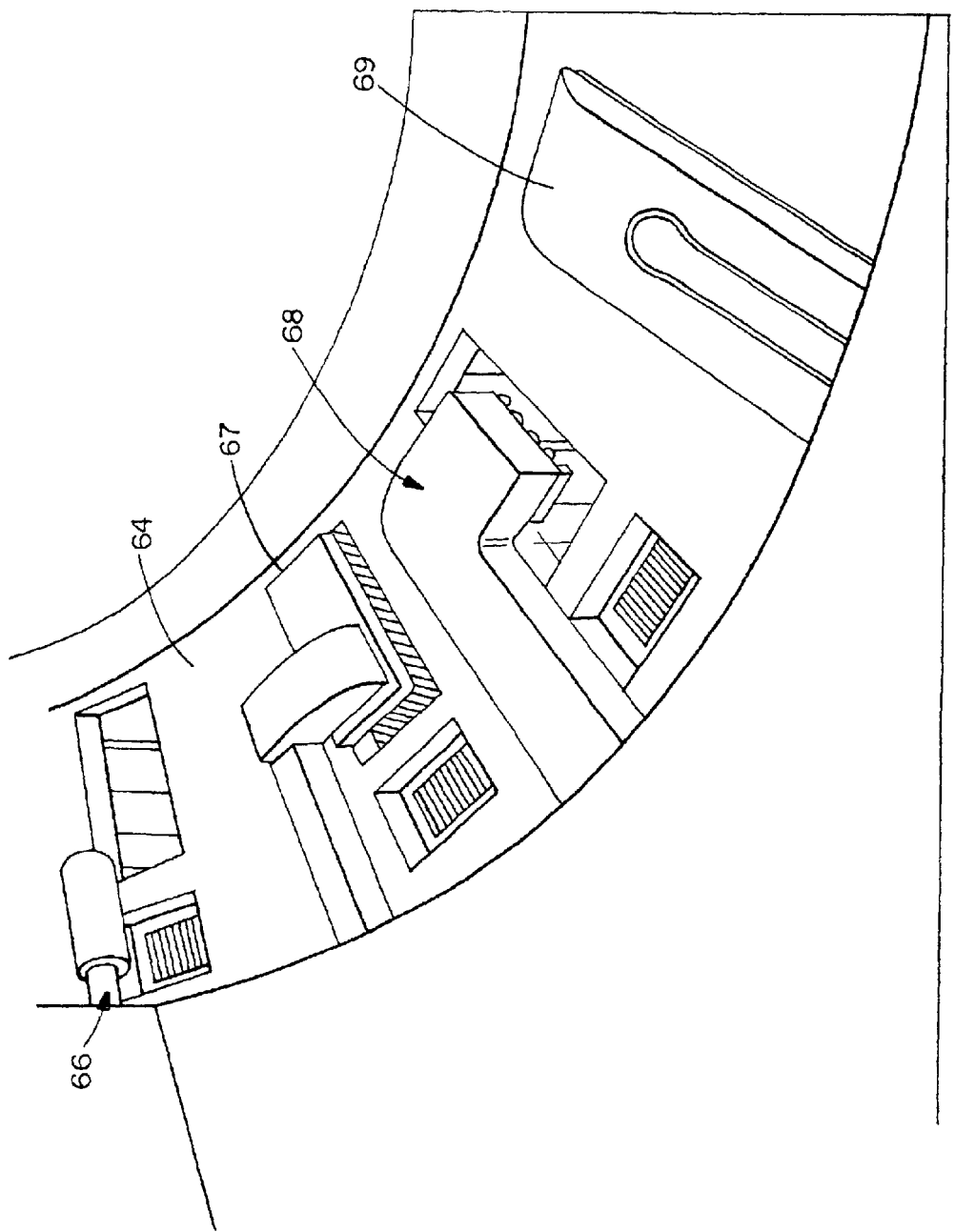
FIG. 13 is a perspective view of the liquid handling zone of the second embodiment of the slide stainer.

FIG. 13 shows the individual mechanisms contained within the liquid handling zone 65, including a hammer 66 for dispensing from cartridge pumps (not shown), an aspiration head 67 for removing liquid from the surface of slides, a bulk liquid dispensing port 68, and an air-mix head 69 for spreading and mixing liquids on the surface of a slide. The electromechanical mechanism for dispensing from cartridge pumps, by compressing a hammer 66 upon a metering chamber of a cartridge pump (not shown in FIG. 13), is similar to the previous embodiment (FIG. 8). Reagent dispensed from the cartridge pump (not shown) flows onto the slide by passing through a roughly rectangular hole in the platen 64.

Figure 14A:
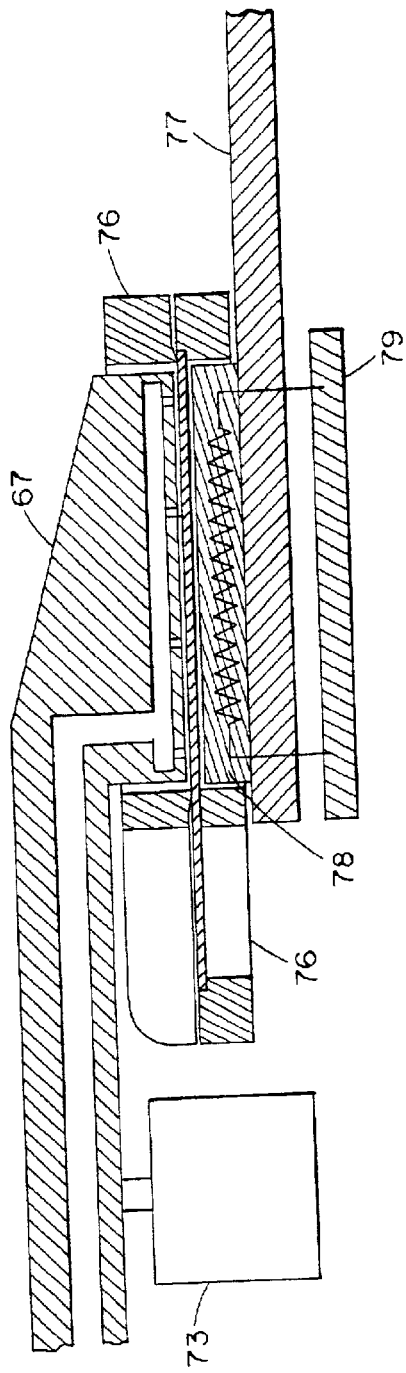
FIGS. 14A and 14B are side cross-sectional views of the liquid aspiration station of the second embodiment, with the aspiration head in the lowered (FIG. 14A) and raised (FIG. 14B) positions.

The aspiration head 67 also functions in a similar manner to that of the previous embodiment. In order to simplify the linkage mechanism for lowering and raising the head 67, the head moves solely in a vertical direction. This is shown in further detail in FIGS. 14A and 14B. FIG. 14A shows a side cross-sectional view of the aspiration head in a down position, within a cavity formed by the microscope slide 75 (bottom surface) and a slide chamber clip 76 (lateral walls). As in the first embodiment, a gasket (not shown) seals the surface where the slide chamber clip 76 contacts the microscope slide 75. A linear stepper motor 73 moves the aspiration head up and down, under computer control (demonstrated schematically in FIG. 15). As in the first embodiment 1, the aspiration head 67 comprises a hollow manifold 74 connected to a source of vacuum. Eight holes communicate between the bottom of the aspiration head 67 and the exterior, through which liquid is aspirated. When vacuum is supplied to the aspiration head 67, and the head 67 is lowered adjacent to the slide, the liquid reagent on top of the slide is aspirated off and collected in a trap bottle 59 (shown schematically in FIG. 15). When the aspiration head 67 is not in use, it is raised to the up position (FIG. 14B), allowing free rotation of the slide rotor 77.

Figure 14B:
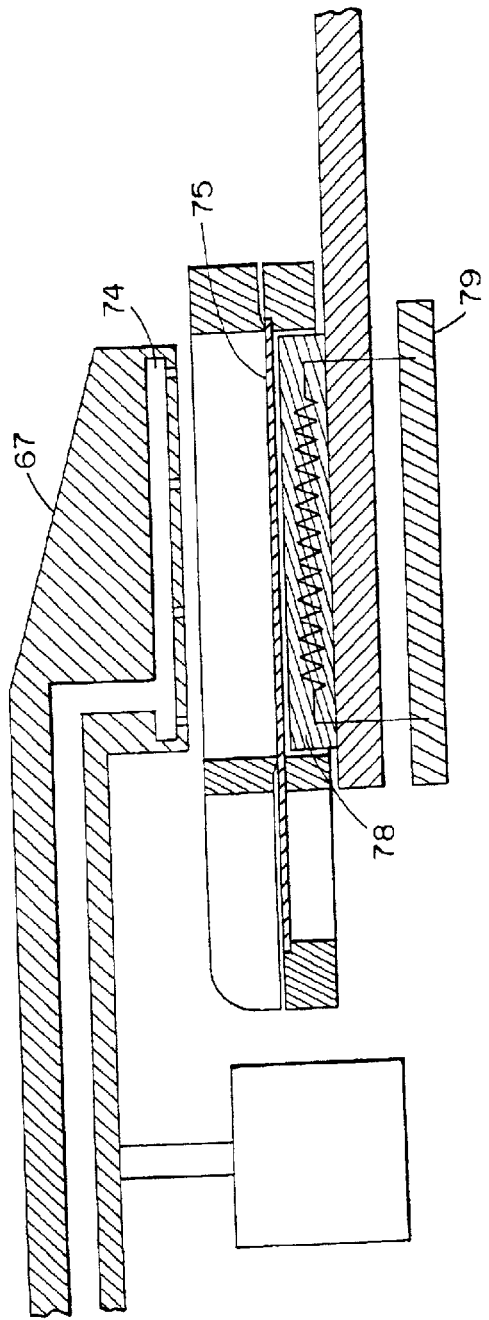

FIGS. 14A and 14B also show the physical location of a heating element 78, represented as a resistive element inside a rectangular box with cross-hatched lines. Each slide rests directly on the heating element 78, so that heat is directly communicated to the microscope slide. A thermistor is incorporated into each heating element (not shown in FIGS. 14A and 14B). Each of forty-nine microscope slides 75 has its own heating element 78, so that the temperature of each slide 75 can be independently regulated. Power for the heating element 78 is supplied directly from a temperature control board 79 that is affixed to the underside of the slide rotor 77. Seven identical temperature control boards 79 are so mounted underneath the slide rotor 77, evenly spaced around the periphery. Each temperature control board supplies power for seven heating elements 78. The means by which this is accomplished is explained later, in reference to FIGS. 17 and 18A–D.

Figure 15:
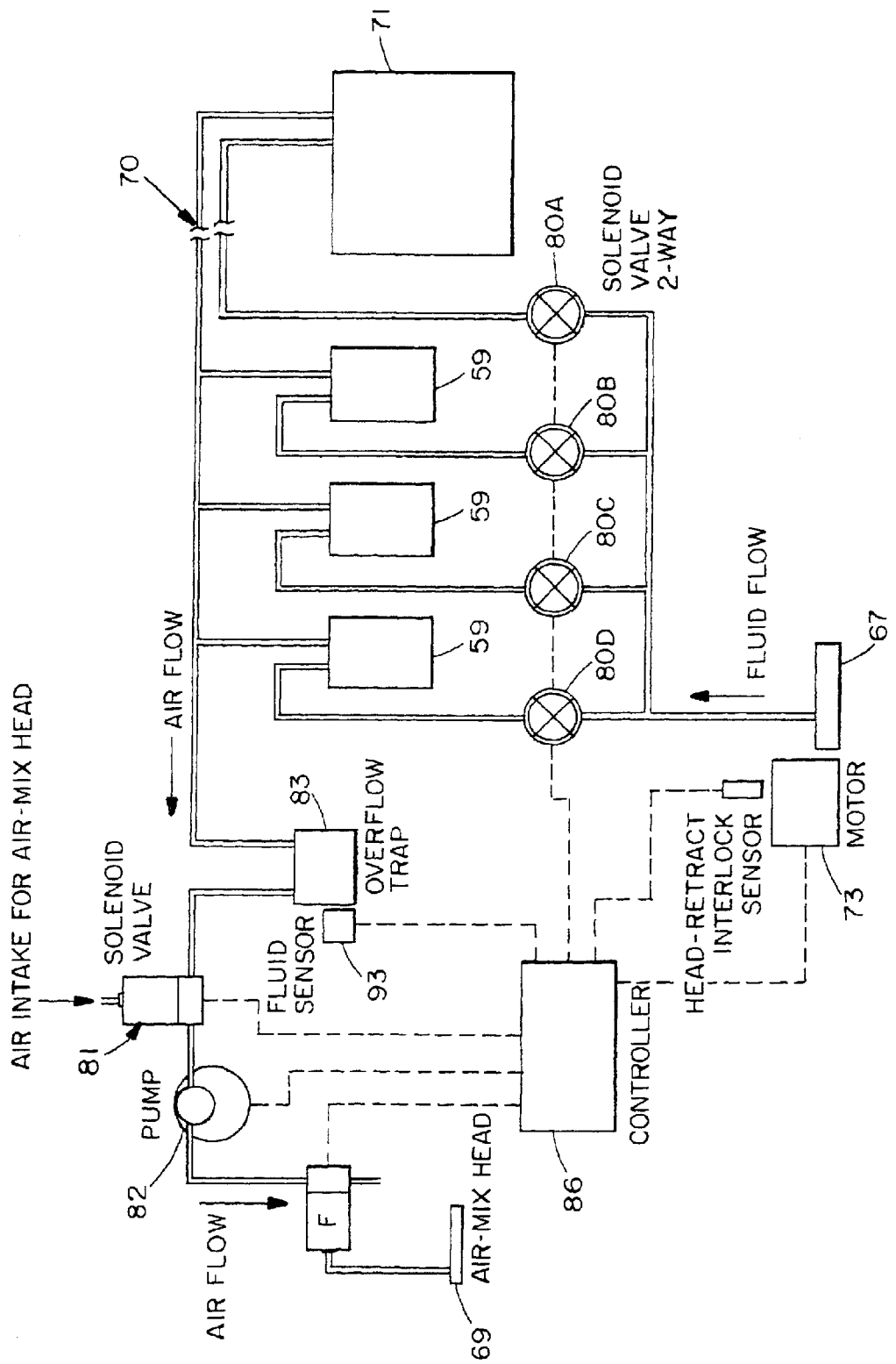
FIG. 15 is a schematic representation of the waste liquid pathways of the second embodiment.

An important aspect of this embodiment, not highlighted in the previous embodiment 1, is the provision for the segregation of waste liquids that are removed from the surface of the slide. A schematic diagram explaining how this is accomplished is shown in FIG. 15. Three different waste bottles 59 are mounted on the instrument. Connections 70 are also provided on the instrument for a large external trap bottle 71, typically of a ten or twenty liter capacity for aqueous waste. Four solenoid valves, labelled 80A–80D control to which bottle aspirated liquid will be directed. These valves are under computer control, schematically represented by the box labelled "controller" 86. Valve 81 is a three way valve. It can allow a direct connection between the vacuum pump 82 and the overflow trap 83, or between the pump and the ambient environment. A connection to the ambient environment is required if the aspiration system needs to be bypassed when the air-mix head 69 is in use. If valves 80A and 81 are appropriately opened, the pump 82 turned on, and the aspirator head 67 lowered so as to aspirate liquid, the liquid will be directed upwards into the tubing, as represented by the arrow "fluid flow." Liquid will then follow the only path available, and be collected into the external trap bottle 71. Valves 80B–80D function similarly for their respective trap bottles 59. A small overflow trap bottle 83 is also inserted into the line with its own fluid sensor 93. This provision is included so as to detect if any of the trap bottles 59, or external trap bottle 71 are overflowing with waste liquid. In that case, liquid would enter the overflow trap bottle and be detected by the fluid sensor. That information would be communicated to the controller 86, which would shut the system down and alert the instrument operator on the computer screen.

Referring to FIG. 13, the liquid handling zone also includes an air-mix head 69. A schematic representation of the air flow into the air-mix head 69 is shown in FIG. 15. The pump generates a high velocity air stream that is channeled into the air-mix head 69. Air intake to the pump is via the three way solenoid valve 81 (FIG. 15). The solenoid valve 81 (FIG. 15) switches so as to channel air directly from the atmosphere to the pump (FIG. 15), bypassing the aspiration system and trap bottles 59 and 71. The high velocity air flow is focused onto the slide. The air-mix head 69 travels back and forth along the length of the slide, pushed and pulled by a belt and pulley that is attached to a motor (not shown). The net effect of this system is to direct a curtain of air back and forth along the length of the slide, causing liquid to be mixed and spread along the surface of the microscope slide.

Figure 16:
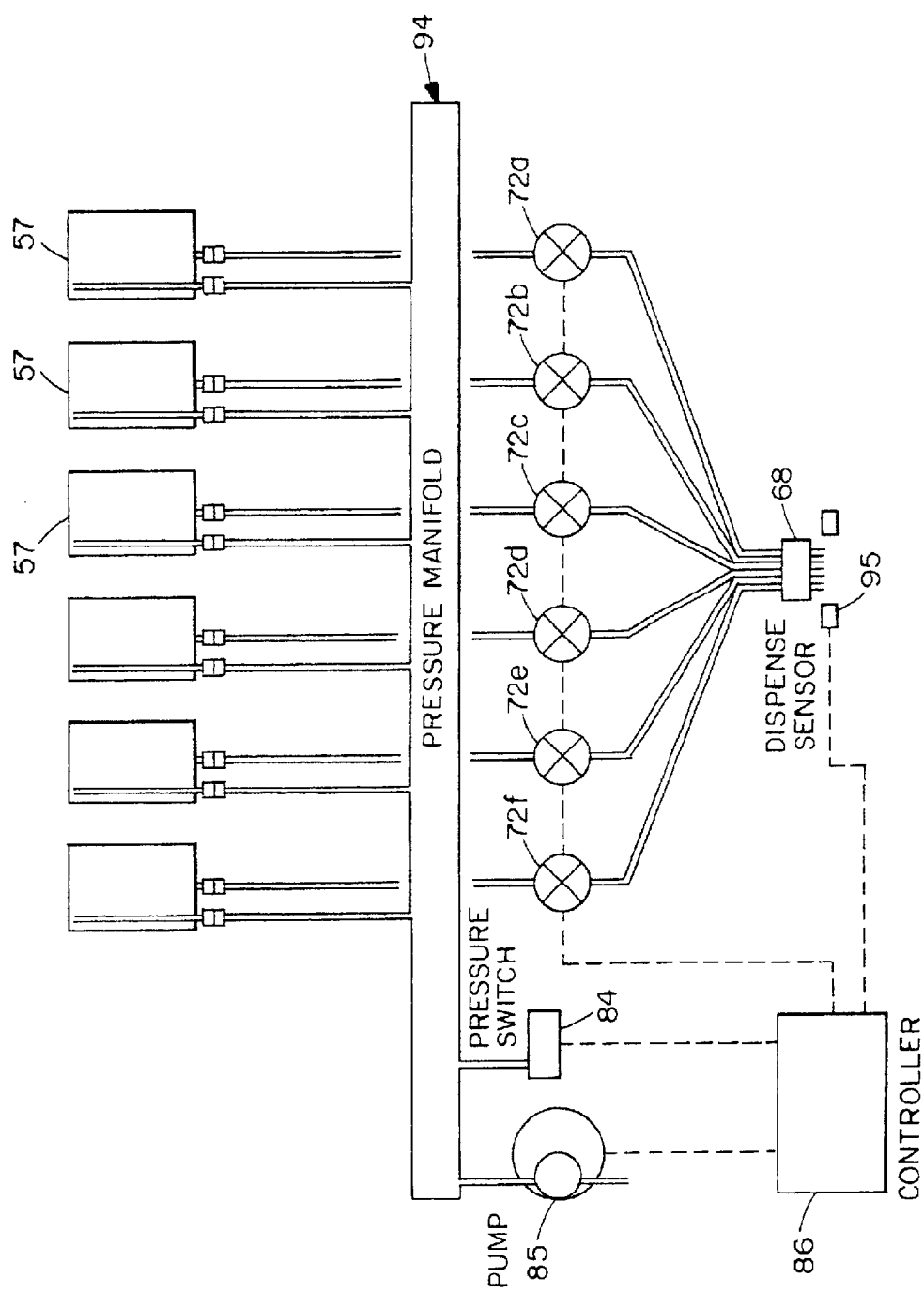
FIG. 16 is a schematic representation of the bulk liquid dispense pathways of the second embodiment.

The liquid handling zone 65 (FIG. 12) includes a bulk liquid dispensing port 68 (FIG. 13). The function of the rinse tubes 28 of the first embodiment 1 (shown in FIG. 1) are all incorporated into a single bulk liquid dispensing port 68 in this preferred embodiment. Therefore, slides are positioned under the bulk liquid dispensing port 68 regardless of the bulk liquid bottle that the liquid is actually derived from. A schematic representation of the fluid pathways and control valves is shown in FIG. 16. The bulk liquid bottles 57 are each connected to a source of pressure, that is generated by a pump 85. The pressure is communicated to the bulk liquid bottles 57 via a pressure manifold 94. Solenoid valves 72a–72f are placed between the bulk liquid dispensing port 68 and each bulk liquid bottle 57. Liquid flows out the bulk liquid dispensing port 68 only when one or more of the valves 72a–72f are open. A pressure switch 84 also communicates with the pressure manifold 94. It is capable of sensing the amount or pressure contained within the manifold 94. When it falls below a specified level, it communicates with the controller 86 causing activation of the pump 85. As the pump generates an increased amount of air pressure within the pressure manifold, the pressure switch resets, causing the pump to stop pumping. In this manner, a relatively constant pressure head is maintained within the pressure manifold 94.

A dispense sensor 95 is positioned underneath the bulk liquid dispensing port 68 to provide verification that liquid was dispensed when one of the solenoid valves 72a–72f were transiently opened. The dispense sensor 95 comprises an optical sensor and an LED light source. When liquid is dispensed from the bulk liquid dispensing port 68, the liquid interrupts the light beam. The change in resistance across the sensor as a result of the decrement in light intensity is communicated to the controller 86.

This second, preferred embodiment of the invention includes the capability to independently heat the forty-nine slides to different temperatures. A novel aspect of this embodiment is the method for independently regulating the amount of power that each of the forty-nine heaters receives. Moreover, each heater also incorporates a temperature sensor. Each of these sensors must communicate with the computer 86 in order to allow for appropriate temperature feedback and regulation. In the first embodiment 1, groups of up to five slides were under a single, common temperature control mechanism. Each heating group had wires that directly connected with the temperature controller (FIG. 7). With three wires per group (power for heat, sensor feedback, and a shared ground) and ten groups of slides, at least thirty wires were contained in the service loop. If a similar system were used for forty-nine different heaters, as in this preferred embodiment, 147 wires would be required in the service loop. Such a bulky service loop would be problematic. Therefore, an alternative method is developed in this preferred embodiment.

Figure 17:
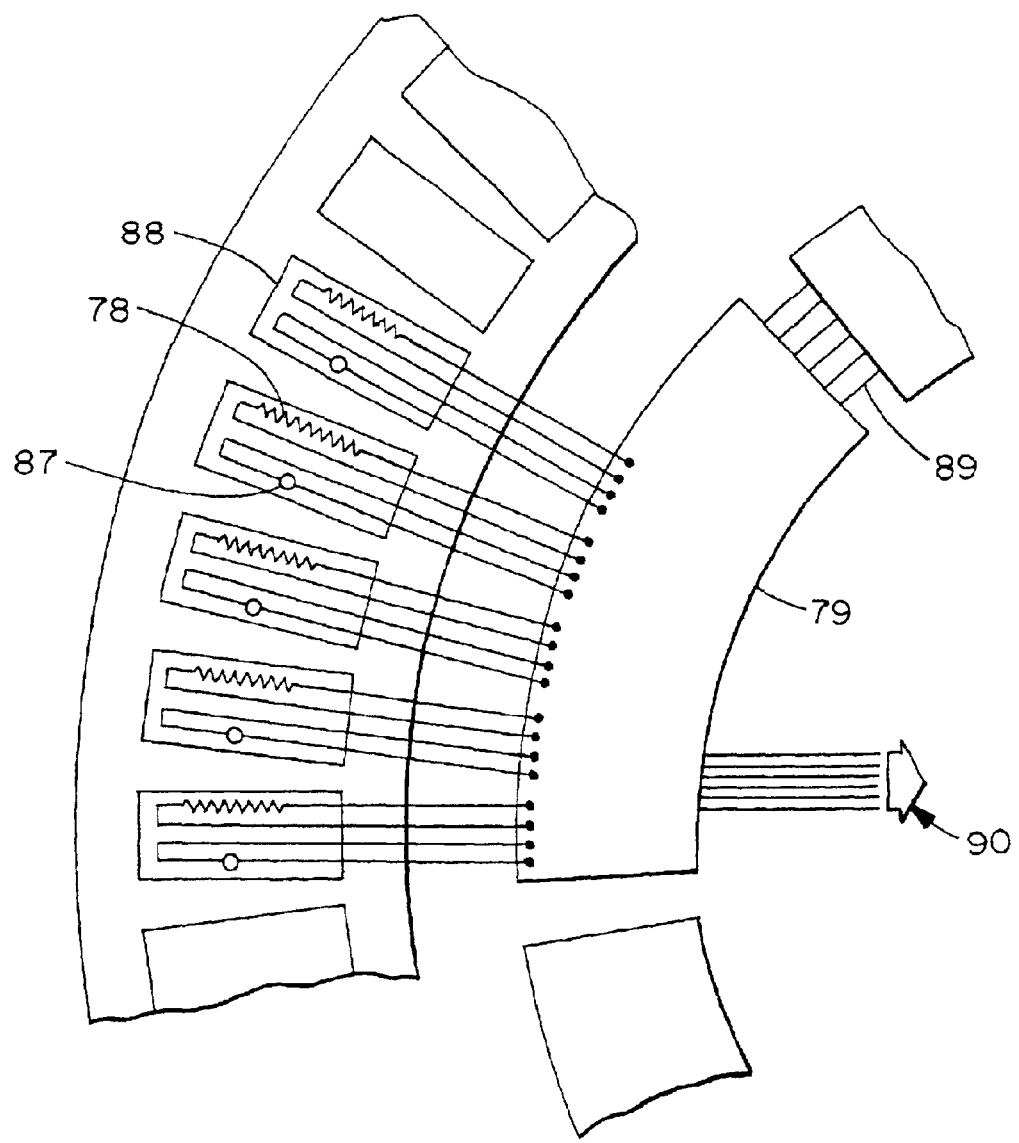
FIG. 17 is a schematic representation of the individual heaters on the slide rotor and the temperature control boards mounted on the slide rotor.
Figure 18A:
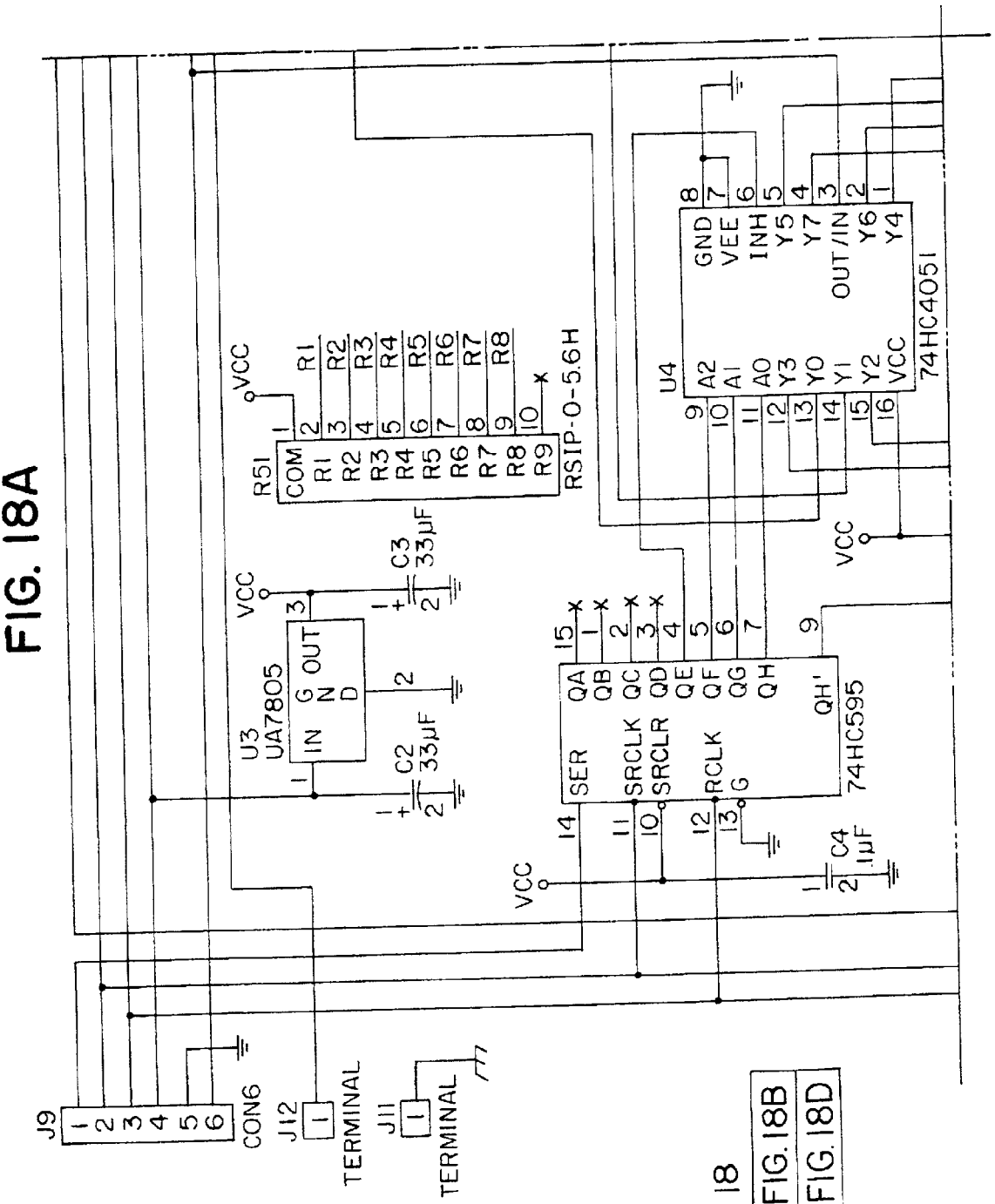
FIGS. 18A–D are a schematic diagram of the electronic circuitry of the temperature control board.
Figure 18B:
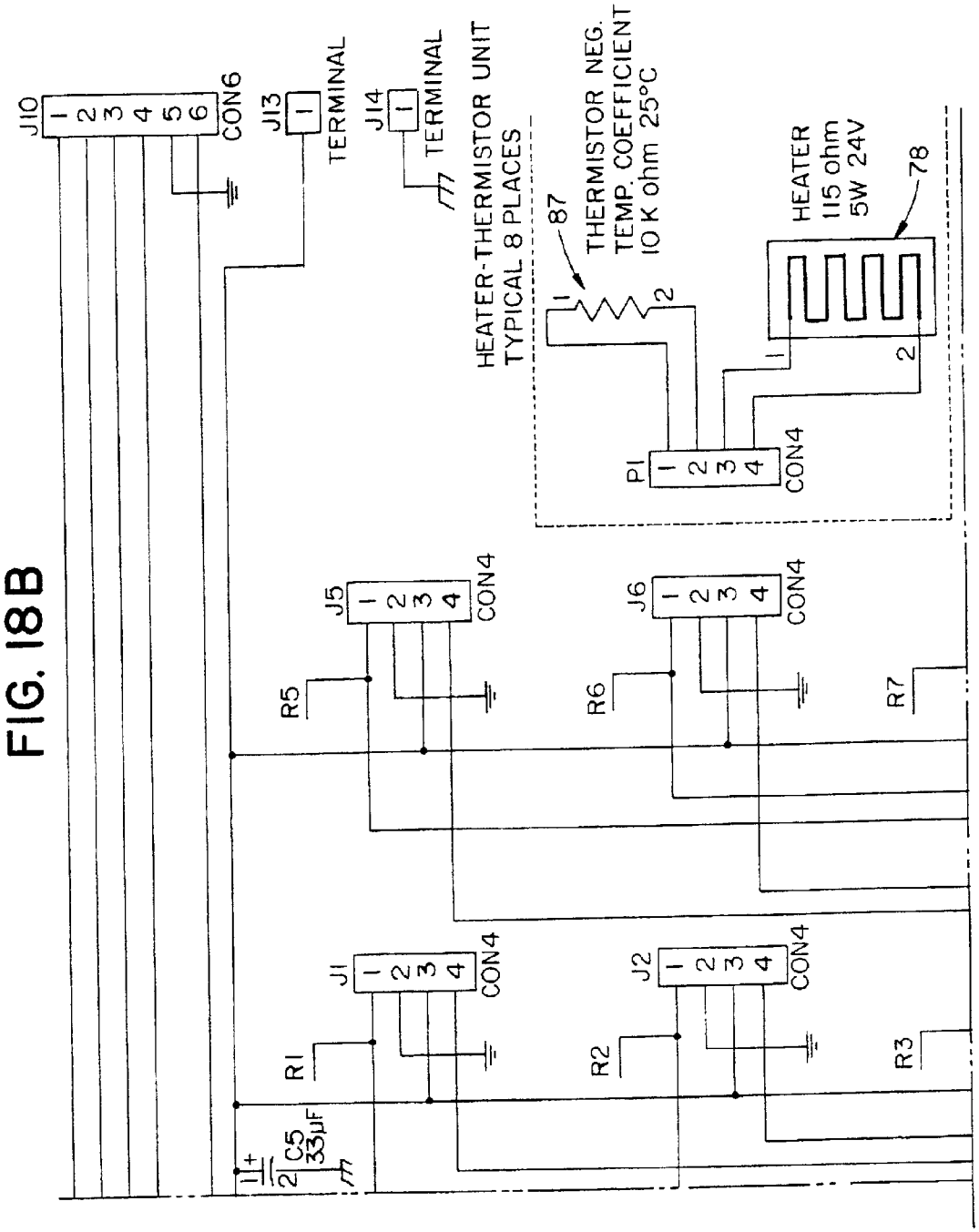
Figure 18C:
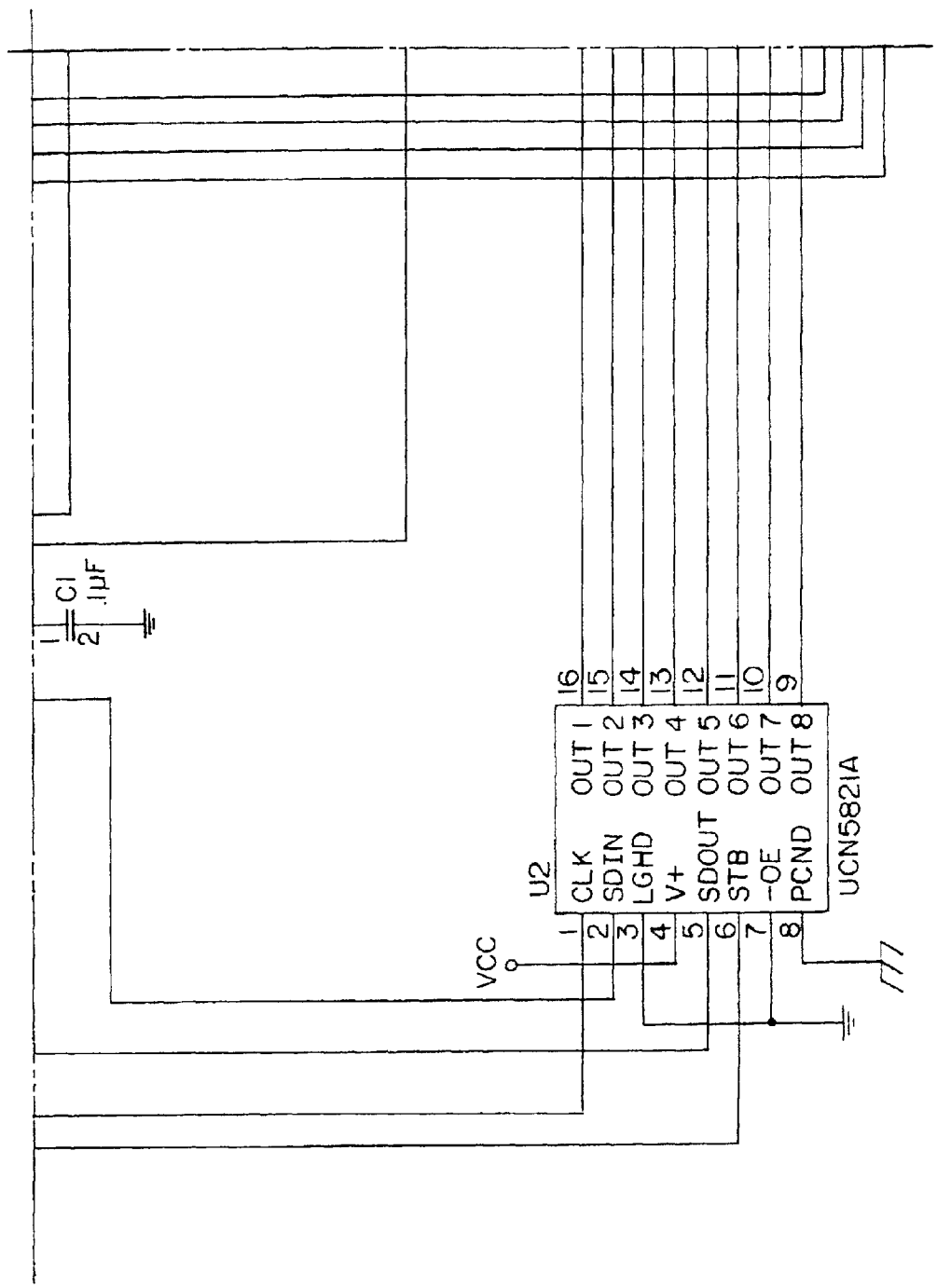
Figure 18D:
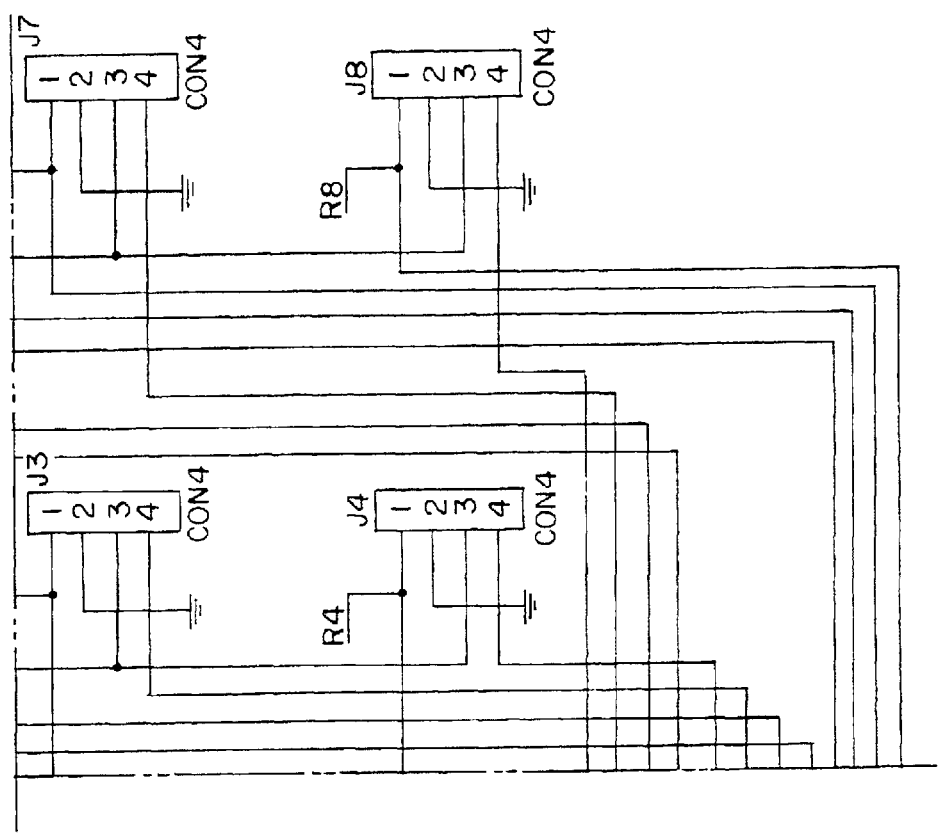

FIG. 17 shows the relationship between each of the heating elements 78 mounted on the slide rotor 77, depicting the heating element 78 as a resistive element. A single sensor 87 is adjacent to each heater. The combination of a single heating element 78 and sensor 87 are so positioned so as to provide a location 88 for a single slide to be heated. The physical layout of this location 88 is demonstrated in FIGS. 14A and 14B. Two wire leads from each heating element 78, and two wire leads from each sensor 87 are connected directly to a temperature control board mounted on the slide rotor 77. Each temperature control board is capable of connecting to up to eight different heater and sensor pairs. Since this embodiment incorporates forty-nine slide positions, seven boards 79 are mounted to the underside of the slide rotor, each connecting to seven heater-sensor pairs. One heater-sensor position per temperature controller board 79 is not used. Also shown in FIG. 17 is the serial connection 89 of each of the seven temperature control boards, in a daisy-chain configuration, by six wires. The first temperature control board is connected via a service loop 90 to the computer 86. The service loop contains only six wires tied together in a harness.

FIGS. 18A–D are an electronic schematic diagram of the temperature control board 79. The design of the temperature control board 79 was driven by the need to minimize the number of wires in the flexible cable (service loop 90) between the heaters and the computer. To minimize the length of wires, seven temperature controller boards 79 are used, each mounted on the slide rotor. Thus, each heater is positioned close to its associated electronics and the size of each board 79 is kept small because each runs only seven heating elements 78. Each temperature controller board 79 includes the function of an encoder and decoder of temperature data. That data relates to the actual and desired temperature of each of heating elements 78. The data flows back and forth between the computer 86 and the temperature control board 79. If an individual heating element 79 requires more or less heat, the computer communicates that information to the temperature control board 79. The temperature control board 79, in turn, directly regulates the amount of power flowing to each heater. By placing some of the logic circuitry on the slide rotor, in the form of the temperature control boards 79, the number of wires in the service loop 90, and their length, are minimized.

In this embodiment, the temperature control board 79 system was designed as a shift register. The machine's controlling microprocessor places bits of data one at a time on a transmission line, and toggles a clock line for each bit. This causes data to be sent through two shift register chips on each control board, each taking eight bits. There are thus 16×7 or 112 bits to be sent out. Referring to FIGS. 18A–D, the data comes in on connector J9.1, and the clock line is J9.2. The shift registers used in this design are "double buffered," which means that the output data will not change until there is a transition on a second clock (R clock), which comes in on pin J9.3. The two clocks are sent to all seven boards in parallel, while the data passes through the shift register chips (U1 and U2) on each board and is sent on from the second shift register's "serial out" pin SDOUT to the input pin of the next board in daisy chain fashion. It will be seen that a matching connector, J10, is wired in parallel with J9 with the exception of pin 1. J10 is the "output" connector, which attaches via a short cable to J9 of the next board in line, for a total of seven boards. The other three pins of J9 are used for power to run the electronics (J9.4), electronic ground (J9.5), and a common return line (J9.6) for temperature measurement function from the sensors.

Of the sixteen data bits sent to each board, eight control the on/off status of up to eight heating elements 78 directly. This can be accomplished with a single chip because shift register U2 has internal power transistors driving its output pins, each capable of controlling high power loads directly. Four of the remaining eight bits are unused. The other four bits are used to select one thermistor 87 out of the machine's total complement of forty-nine. For reasons of economy and to reduce the amount of wiring, the instrument has only one analog-to-digital converter for reading the forty-nine temperature transducers (thermistors 87), and only one wire carrying data to that converter. This channel must therefore be shared between all of the transducers (thermistors 87), with the output of one of them being selected at a time. Component U4 is an analog multiplexer which performs this function. Of the four digital bits which are received serially, one is used to enable U4, and the other three are used to select one of the component's eight channels (of which only seven are used). If pin four is driven low, U4 for that board 79 becomes active and places the voltage from one of the seven channels of that board on the shared output line at J9.6. Conversely, if pin four is pulled high, U4's output remains in a high impedance state and the output line is not driven. This allows data from a selected board 79 to be read, with the remaining boards 79 having no effect on the signal. Multiplexer U4 can only be enabled on one board 79 at a time; if more than one were turned on at a time, the signals would conflict and no useful data would be transmitted.

Temperature sensing is accomplished by a voltage divider technique. A thermistor 87 and a fixed resistor (5.6 kilohms, R1–R8, contained in RS1) are placed in series across the 5 volt electronic power supply. When the thermistor is heated, its resistance drops and the voltage at the junction point with the 5.6 kilohm resistor will drop.

There are several advantages to the design used in this embodiment. Namely, the temperature control boards 79 are small and inexpensive. Moreover, the heater boards are all identical. No "address" needs to be set for each board 79. Lastly, the service loop 90 is small in size.

An alternative potential design is that each temperature control board 79 could be set up with a permanent "address" formed by adding jumper wires or traces cut on the board. The processor would send out a packet of data which would contain an address segment and a data segment, and the data would be loaded to the board whose address matched the address sent out. This approach takes less time to send data to a particular board, but the address comparison takes extra hardware. It also demands extra service loop wires to carry the data (if sent in parallel) or an extra shift register chip if the address is sent serially. As yet another potential design is that each temperature control board 79 could have its own microprocessor. They could all be connected via a serial data link to the main computer 86. This approach uses even fewer connecting wires than the present embodiment, but the cost of hardware is high. It also still implies an addressing scheme, meaning that the boards would not be identical. Also, code for the microprocessors would be required.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. A microscope slide stainer, comprising:
   a moving platform adapted to support a plurality of microscope slides bearing biologic samples;
   a plurality of heating elements, each heating at least one slide, the heating elements heating the slides to different temperatures;
   electronic circuitry that supplies variable amounts of electrical power to said heating elements, said electronic circuitry being mounted on the moving platform; and
   a user interface through which desired temperatures for microscope slides are specified, said user interface being mounted off of the moving platform and communicating data to said electronic circuitry on the moving platform to cause said electronic circuitry on the moving platform to supply electrical power to said heating elements to heat said heating elements to said desired temperatures.

2. A microscope slide stainer as claimed in claim 1, wherein said electronic circuitry on the moving platform and the user interface, not mounted on said moving platform, communicate electrically via a group of conductors.

3. A microscope slide stainer as claimed in claim 2, wherein the number of conductors in the group of conductors is fewer than the number of heating elements.

4. A microscope slide stainer as claimed in claim 1, wherein said electronic circuitry comprises a shift register, which receives control data from the user interface.

5. A microscope slide stainer as claimed in claim 1, further comprising a temperature sensor for providing temperature feedback information.

6. A microscope slide stainer as claimed in claim 1 wherein each heating element heats a single slide.

7. A microscope slide stainer as claimed in claim 1 wherein each heating element comprises a flat slide support surface.

8. A microscope slide stainer, comprising:
   a plurality of microscope slides bearing biologic samples, positioned on a moving platform;
   a plurality of heating elements on the moving platform, each element heating at least one slide, and at least one being heated to a temperature distinct from the temperatures of other heating elements;

electronic circuitry that regulates electrical power to said heating elements, said electronic circuitry being mounted on the moving platform;

a user interface through which desired temperatures for microscope slides is specified, said user interface being mounted off of the moving platform and said user interface comprising electronic circuitry which communicates data to the electronic circuitry on the moving platform, causing said electronic circuitry on the moving platform to supply electrical power to said heating elements to attain said desired temperature; and, a group of conductors for providing an electrical connection between said electronic circuitry on the moving platform and the user interface, the number of conductors in said group of conductors being less than the number of heater elements.

9. A microscope slide stainer as claimed in claim 8, further comprising a temperature sensing means for providing temperature feedback data.

10. An automated device for preparation or incubation of biologic samples, comprising:

a moving platform adapted to support a plurality of biologic samples;

a plurality of heaters positioned on the moving platform so as to provide heat to one or more samples;

a processor that specifies the desired temperatures for the heaters, said processor being mounted off of the moving platform;

independent heating control capable of heating the heaters to different temperatures, said heating control comprising:

electronic circuitry mounted on the moving platform supplying electrical power to at least one heater; and a data communication link between the processor and said electronic circuitry mounted on the moving platform, through which said electronic circuitry receives data from the processor to cause said electronic circuitry to provide an appropriate amount of electrical power to each of said heaters to heat the heaters to the processor-specified temperatures.

11. An automated device, as claimed in claim 10, wherein the biologic samples are mounted on a microscope glass slide.

12. An automated device, as claimed in claim 10, further comprising a temperature sensor that provides temperature feedback information.

13. A microscope slide stainer, comprising:

a moving platform adapted to support a plurality of microscope slides bearing biological samples;

a plurality of heating means, each for heating at least one slide, each of the heating means having the capability of heating to different temperatures;

electronic circuitry means for regulating electric power to the heating means, said electronic circuitry means being mounted on the moving platform; and user interface means in communication with the electronic circuitry means for specifying a desired temperature for each microscope slide, said user interface means being mounted off of the moving platform and communicating data to the electronic circuitry on the moving platform to regulate the electrical power to the heating means.

* * * * *